United States Patent [19]

Sugimoto et al.

[11] Patent Number: 5,278,059
[45] Date of Patent: Jan. 11, 1994

[54] POLYPEPTIDE POSSESSING CYCLOMALTODEXTRIN GLUCANOTRANSFERASE ACTIVITY

[75] Inventors: Toshiyuki Sugimoto; Michio Kubota; Shuzo Sakai, all of Okayama, Japan

[73] Assignee: Kabushiki Kaisha Hayashibara Seibutsu Kagaki Kenkyujo, Okayama, Japan

[21] Appl. No.: 794,347

[22] Filed: Nov. 12, 1991

Related U.S. Application Data

[63] Continuation of Ser. No. 438,933, Nov. 22, 1989, abandoned, which is a continuation of Ser. No. 804,487, Dec. 4, 1985, abandoned.

[51] Int. Cl.$^5$ .......................... C12N 9/10; C12N 15/54
[52] U.S. Cl. ............................... 435/193; 435/252.31; 435/252.33; 435/97; 536/23.3
[58] Field of Search ...................... 435/97, 193, 252.31, 435/252.33; 536/27, 23.3

[56] References Cited

U.S. PATENT DOCUMENTS 4,317,881  3/1980  Yagi et al. ............................ 435/97

FOREIGN PATENT DOCUMENTS

| | | |
|---|---|---|
| 2246638 | 8/1975 | European Pat. Off. . |
| 0057976 | 8/1982 | European Pat. Off. . |
| 2213340 | 10/1974 | France . |
| 2253831 | 9/1975 | France . |
| 1414235 | 11/1975 | United Kingdom . |
| 1442480 | 7/1976 | United Kingdom . |
| 1447492 | 8/1976 | United Kingdom . |
| 1459654 | 12/1976 | United Kingdom . |
| 2091268 | 7/1982 | United Kingdom . |

OTHER PUBLICATIONS

Chemical Abstracts, vol. 105, No. 21, Nov. 24, 1986, p. 595, resume' No. 189477m, Columbus, Ohio, U.S.; & JP-A-61 132 178 (National Institute of Food Research) Jun. 19, 1986.
Chemical Abstracts, vol. 105, No. 21, Nov. 24, 1986, p. 595, resume' no. 189478n, Columbus, Ohio, U.S.; & JP-A-61 132 183 (National Institute of Food Research) Jun. 19, 1986.
T. Maniatis et al: "Molecular cloning: A Laboratory Manual", 1982, pp. 296-306, Cold Spring Harbor Laboratory, New York US; "Construction of Genomic libraries in cosmid vectors".
Kitahata, S. (1982) Chem, Abs. vol. 97, 35250m.
Maniatis, T. et al. Molecular Cloning, A Laboratory Manual, Cold Spring Harbor Laboratory, 1982, p. 5.
Kobayashi, S., et al. (1978) Carbohydr. Res 61,229-238.
Gryczan, T. J., et al. (1978) J. Bacteriol. 134, 318-329.
Chem. Abs. (1982) vol. 96, 138639d.
Kitahata, S., et al. (1982) J. Jap. Soc. Starch Sci. 29(1), 7-12.
Suggs, S. V., et al. (1981) Proc. Natl Acad, Sci., USA 78(11), 6613-6617.

*Primary Examiner*—Charles L. Patterson, Jr.
*Attorney, Agent, or Firm*—Browdy and Neimark

[57] ABSTRACT

The sequence of cyclomaltodextrin glucanotransferase (CGTase) gene derived from a microorganism of genus Bacillus and the amino acid sequence of CGTase are determined. A recombinant DNA carrying the CGTase gene is introduced by in vitro genetic engineering technique into a host microorganism of species *Bacillus subtilis* or *Escherichia coli.* The recombinant microorganism carrying the recombinant DNA autonomically proliferates to secrete a large amount of CGTase.

25 Claims, 16 Drawing Sheets

FIG. 5A

```
  10          20          30          40          50          60
GCTGGAAATC  TTAA TAAGGT  AAACT TTACA  TCAGATG TTG  TCTATCAAAT  TGTAGTGGAT 70          80          90         100         110         120
CGAT TTGTGG  ATGGAAATAC  ATCCAA TAAT  CCGAGTGGAG  CATTATTTAG  CTCAGATGT 130         140         150         160         170         180
ACGA ATTTAC  GCAAGTATTG  CGGTGGAGAT  TGGCAAGGCA  TA TCAAT AA  AAT TAACGAT 190         200         210         220         230         240
GGGTAT TTAA  CAGATATGGG  TGTGACAGCG  ATAT GGATTT  CTCAGCCTGT  AGAAAATGTA 250         260         270         280         290         300
TT TTCTGTGA  TGAATGATGC  AAGCGGTTCC  GCATCCTATC  ATGG TTATTG  GGCGCGCGAT 310         320         330         340         350         360
TTCAAAAAGC  CAAACCCGTT  TT TTGGTACC  CTCAGTGATT T  TCCAACGTTT  AGTTGATGCC 370         380         390         400         410         420
GCACATGCAA  AAGGAATAAA  GGTAATTATT  GAC TTTGCCC  CCAACCATAC  TTCTCCTGCT 430         440         450         460         470         480
TCAGAAACGA  AT CCT TCTTA  TATGGAAAAAC  GGACGACTGT  ACGATAATGG  GACATTGCTT 490         500         510         520         530         540
GGCGGTTACA  CAAATGATGC  CAACATGTAT  T TTCACCA TA  ACGGTGGAAC  AACGTTTTCC
```

FIG. 5B

```
       550              560              570              580              590              600
AGCTT AGAGG    ATGGGATTTA    TCGAAATCTG    TTTGACT TGG    CGGACCTTAA    CCATCAGAAC 610              620              630              640              650              660
CCTGT TA TTG   ATAGG TATTT   AAAAGATGCA    GTAAAAA TGT   GGA TAGATAT    GGGGATTGAT 670              680              690              700              710              720
GGTAT CCGTA    TGGATGCGGT    GAAGCACATG    CCGTTTG GAT   GGCAAAAATC    TCTGATGGAT 730              740              750              760              770              780
GAGAT TGATA    AC TATCGTCC   TGTCTTTACG    TT TGGGGAGT   GG TTTTTGTC   AGAAAATGAA 790              800              810              820              830              840
GTGGACGCGA    ACAATCAT TA   CTTTGCCAAT    GAAAGTGG AA   TGAGT TTGCT   CGAT TTCGT 850              860              870              880              890              900
TTCGGACAAA    AGCTTCGTCA    AGTATTGCGC    GACGAGGTTC    ATAAT TGGTA   TGGC TTTAAT 910              920              930              940              950              960
CAAATGATTC    AAGATACGGC    ATCAGCATAT    GACGGAGGAG    TCG ATCAAGT   AACAT TCATA 970              980              990             1000             1010             1020
GACAACCATG    AT ATGGATCG   GTT TATGATT   GACGGAGGAG    ATCCGGCAA     GGTGGATATG 1030             1040             1050             1060             1070             1080
GCACTTGCTG    TA TTATTGAC   ATCCCGTGGC    GTACCGAA TA   T TTACTATGG   TACAGAGCAA
```

FIG. 5C

```
      1090          1100          1110          1120          1130          1140
TACATGACCG    GTAACGGCGA    TCCAAACAAT    CGTAAGATGA    TGAGTTCATT    CAA TAAAAAT 1150          1160          1170          1180          1190          1200
ACTCGCGCGT    ATCAAGT GAT    TCAAAAACTA    TCT TCTCTCC    GACGAAACAA    TCCGGGCGTTA 1210          1220          1230          1240          1250          1260
GCT TATGGTG    ATACGGAACA    GCGTTGGATC    AATGGCGATG    TG TATGTGT A    TGAGCGACAG 1270          1280          1290          1300          1310          1320
T TTGGCAAAG    ATG TTGTGTT    AGTT CGGGTT    AATCGT AGTT    CAAGCAGTAA    TTAC TCGATT 1330          1340          1350          1360          1370          1380
ACTGGC TTAT    TTACAGCTTT    ACCAGCAGGA    ACATATACGG    ATCAGCT TGG    CGGTC TTTTA 1390          1400          1410          1420          1430          1440
GACGGAAATA    CAA TTCAAGT    CGGTTCAAAT    GGATCAGT TA    ATGCATT TGA    CTTAGGACCG 1450          1460          1470          1480          1490          1500
GGGGAAGTCG    GTGTATGGGC    ATACAGTGCA    ACAGAAAGCA    CGCCAATTAT    TGGTCATGT T 1510          1520          1530          1540          1550          1560
GGACCGATGA    TGGGGCAAGT    CGGTCATCAA    GTAACCATTG    ATGGGCGAAGG    ATTCGGAACA 1570          1580          1590          1600          1610          1620
AATACGGGCA    CTGTGAAGTT    CGGAACGGACA    GCTGCCAATG TTGTG TCT TG    GTCTAACAAT
```

FIG. 5D

```
1630       1640       1650       1660       1670       1680
CAAATCGTTG TGGCTGTACC AAATGTG TCA CCAGGAAAAT ATAATATTAC CGTCCAATCA 1690       1700       1710       1720       1730       1740
TCAAGCGGTC AAACGGAGTGC GGCTTATGAT AAC TTTGAAG TACTAACAAA TGATCAAGTG 1750       1760       1770       1780       1790       1800
TCAGTGCGGT TTGT TGTTAA TAACGCGACT ACCAATCTAG GGCAAAA TAT ATACATTG TT 1810       1820       1830       1840       1850       1860
GGCAACGTAT ATGAGCTCGG CAACTGGGAC ACTAGTAAGG CAATCGGTCC AATGT TCAAT 1870       1880       1890       1900       1910       1920
CAAGTGGGT TT ACTCCTATCC TACATGGTA T ATAGATGTCA GTGTCCCAGA AGGAAAGACA 1930       1940       1950       1960       1970       1980
ATT GAGTT TA AGT TTATTAA AAAAGACAGC CAAGGTAATG TCACTTGGGA AAGTGGTTCA 1990       2000       2010       2020       2030       2040
AATCATG TT T ATACGACACC AACGAATACA ACCGGAAAAA TTATAGTGGA TTGGCAGAAC
```

FIG. 6

```
         10         20         30         40         50         60
ATGAGAAGAT GGC TTTCGCT AGTC TTGAGC ATGTCATTTG TATTAGTGC AATTTTATA
         70         80         90        100
GTATCT GATA CGCAGAAAGT CACCGTTG AA GCA
```

FIG. 7

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1> | Met | Arg | Arg | Trp | Leu | Ser | Leu | Val | Leu | Ser | Met | Ser | Phe | Val | Phe |
| 16> | Ser | Ala | Ile | Phe | Ile | Val | Ser | Asp | Thr | Gln | Lys | Val | Thr | Val | Glu |
| 31> | Ala |

FIG. 8A

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1> | Ala | Gly | Asn | Leu | Asn | Lys | Val | Asn | Phe | Thr | Ser | Asp | Val | Val | Tyr |
| 16> | Gln | Ile | Val | Val | Asp | Arg | Phe | Val | Asp | Gly | Asn | Thr | Ser | Asn | Asn |
| 31> | Pro | Ser | Gly | Ala | Leu | Phe | Ser | Ser | Gly | Cys | Thr | Asn | Leu | Arg | Lys |
| 46> | Tyr | Cys | Gly | Gly | Asp | Trp | Gln | Gly | Ile | Ile | Asn | Ala | Ile | Asn | Asp |
| 61> | Gly | Tyr | Leu | Thr | Asp | Met | Gly | Val | Thr | Ala | Asp | Lys | Ile | Asn | Asp |
| 76> | Pro | Val | Glu | Asn | Val | Phe | Ser | Val | Thr | Ala | Ile | Trp | Ile | Ser | Gln |
| 91> | Ala | Ser | Tyr | His | Gly | Tyr | Phe | Ala | Met | Asn | Asp | Ala | Ser | Gly | Ser |
| 106> | Pro | Phe | Phe | Gly | Thr | Leu | Trp | Asp | Arg | Asp | Phe | Lys | Leu | Pro | Asn |
| 121> | Ala | His | Ala | Lys | Gly | Ile | Ser | Val | Ile | Gln | Arg | Leu | Val | Asp | Ala |
| 136> | His | Thr | Ser | Pro | Ala | Ser | Lys | Thr | Asn | Ile | Asp | Phe | Ala | Pro | Asn |
| 151> | Gly | Arg | Leu | Pro | Tyr | Asn | Glu | Thr | His | Leu | Pro | Ser | Met | Glu | Asn |
| 166> | Asp | Ala | Asn | Met | Asp | Phe | Gly | Tyr | Leu | Gly | Ser | Tyr | Tyr | Thr | Asn |
| 181> | Ser | Leu | Glu | Gln | Tyr | Ile | Gly | His | Arg | Arg | Gly | Thr | Thr | Phe | Ser |
| 196> | Leu | Asn | His | Asp | Asn | Pro | Ile | Arg | Asn | Leu | Phe | Asp | Leu | Ala | Asp |
| 211> | Val | Lys | Met | Trp | Ile | Asp | Met | Gly | Ile | Asp | Tyr | Leu | Ile | Asp | Ala |
| 226> | Ala | Val | Lys | His | Met | Pro | Tyr | Gly | Trp | Asp | Gly | Ile | Met | Met | Asp |
| 241> | Glu | Ile | Asp | Asn | Tyr | Pro | Pro | Val | Phe | Thr | Phe | Gly | Glu | Trp | Phe |
| 256> | Leu | Ser | Glu | Asn | Ile | Asp | Asp | Ala | Asn | Asn | Phe | Gly | Glu | Trp | Phe |
| 271> | Glu | Ser | Gly | Met | Ser | Val | Asp | Ala | Asn | Arg | His | Tyr | Phe | Ala | Asn |
| 286> | Arg | Gln | Val | Leu | Arg | Leu | Leu | Asp | Phe | Asn | Phe | Gly | Gln | Lys | Leu |
| 301> | Gln | Met | Ile | Arg | Asn | Asn | Asn | Ser | Asp | Asn | Trp | Tyr | Gly | Phe | Asn |
| 316> | Gln | Met | Ile | Gln | Asp | Thr | Ala | Ser | Ala | Tyr | Asp | Glu | Tyr | Val | Asp |
| 331> | Asp | Gly | Gly | Asp | Pro | Arg | Lys | Val | Asp | Met | Ala | Arg | Ala | Leu | Met |
| 346> | Leu | Thr | Ser | Arg | Gly | Val | Pro | Asn | Ile | Tyr | Tyr | Gly | Thr | Glu | Gln |
| 361> | Tyr | Met | Thr | Gly | Asp | Gly | Asp | Pro | Asn | Asn | Arg | Gly | Met | Met | Ser |
| 376> | Ser | Phe | Asn | Lys | Asn | Thr | Arg | Ala | Tyr | Gln | Val | Ile | Gln | Lys | Leu |

FIG. 8B

| | | | | | | Asn | Pro | Ala | Leu | Ala | Tyr | Gly | Asp | Thr |
|---|---|---|---|---|---|---|---|---|---|---|---|---|---|---|
| 391> | Ser | Ser | Leu | Arg | Arg | Asn | Gly | Asp | Val | Tyr | Val | Tyr | Glu | Arg | Gln |
| 406> | Glu | Gln | Arg | Trp | Ile | Asn | Leu | Val | Arg | Asn | Ala | Leu | Ser | Ser | Ser |
| 421> | Phe | Gly | Lys | Asp | Val | Val | Gly | Leu | Phe | Thr | Ala | Pro | Gly | Ala | Gly |
| 436> | Ser | Asn | Tyr | Ser | Ile | Thr | Gly | Leu | Asp | Gly | Leu | Asn | Thr | Ile |
| 451> | Thr | Tyr | Thr | Asp | Leu | Gly | Ser | Val | Tyr | Ser | Ala | Ala | Asp | Gly | Pro |
| 466> | Gln | Val | Gly | Tyr | Asp | Gly | Ala | Tyr | Ser | Met | Thr | Gly | Ser | Thr | Gln |
| 481> | Gly | Glu | Glu | Gly | Ser | Val | Pro | Met | Phe | Gly | Thr | Gly | Val | Gly | Val |
| 496> | Ile | Ile | Ile | Gly | Gly | Glu | Gly | Phe | Asn | Ala | Gly | Thr | Trp | His | Gln |
| 511> | Val | Thr | Thr | Asp | Thr | Ala | Ala | Pro | Asn | Val | Thr | Val | Thr | Thr | Val |
| 526> | Lys | Phe | Val | Val | Val | Val | Pro | Ser | Ser | Pro | Gly | Lys | Ser | Asn | Asn |
| 541> | Gln | Ile | Gln | Gln | Ser | Ser | Ser | Asn | Ser | Val | Ala | Lys | Ala | Tyr | Asp |
| 556> | Ile | Thr | Val | Val | Leu | Thr | Asn | Gly | Asn | Ser | Ile | Tyr | Arg | Phe | Val |
| 571> | Asn | Phe | Ala | Gln | Thr | Thr | Gly | Gln | Thr | Ile | Ile | Phe | Ile | Ala | Val |
| 586> | Val | Asn | Ala | Tyr | Glu | Leu | Val | Trp | Asp | Tyr | Ser | Pro | Thr | Trp | Ile |
| 601> | Gly | Asn | Val | Phe | Ile | Pro | Val | Tyr | Lys | Asp | Tyr | Pro | Glu | Lys | Tyr |
| 616> | Gly | Pro | Met | Ser | Ala | Leu | Gly | Lys | Ser | Thr | Ile | Trp | Glu | Ser | Phe |
| 631> | Ile | Asp | Val | Asp | Ser | Asn | Val | Asn | Val | Leu | Pro | Phe | Lys | Gly | Ser |
| 646> | Ile | Lys | Lys | Tyr | Thr | Val | Gly | Asn | Pro | Gln | Asp | Glu | Thr | Lys | Gln |
| 661> | Asn | His | Val | Gln | Ser | Asn | Pro | Asn | Thr | Pro | Trp | His | Tyr | Gly | Ser |
| 676> | Val | Asp | Asp | Gln | Thr | Asn | Pro | Thr | Thr | Thr | Thr | Gly | Ile | Ile | Ile |

FIG. 9A

```
         10         20         30         40         50         60
TCCCCGGATA CGAGCGTGAA CAACAAGCTC AAT TTAGCA CGGA TACGGT T TACCAGATT
         70         80         90        100        110        120
GTAACCGACC GGTTTGTGGA CGGCAAT TCC GCCAACAACC CGACCGGAGC AGCCTTCAGC
        130        140        150        160        170        180
AGCGATCA TT CCAACCTGAA GCTGTATTTC GGGGGGCGACT GGCAGGGGAT CACGAACAAA
        190        200        210        220        230        240
ATCAACGACG GCTATCTGAC CGGAATGGGC ATCACCGCCC TCTGGA TCTC GCAGCCGGTT
        250        260        270        280        290        300
GAGAACATCA CCGCCCGTCAT CAATTA TTCG GGCGTCAACA ATACAG CTTA CC ACGGTTAC
        310        320        330        340        350        360
TGGCCCTCGCG ACTTCAAGAA GACCAATGCC GCGTTCGGCA GCTTCACCGA CT TC TCCAAT
        370        380        390        400        410        420
TTGATCGCCG CAGGCGCATTC ACACAATATC AAGGTAGT TA TGGACTT TGC ACCT AATCAC
        430        440        450        460        470        480
ACCAACCCGG CTTCGAGTAC GGACCCCTCG TTCGCCGAGA ACGGCGCGCT CTACAACAAC
        490        500        510        520        530        540
GGAACGCTGC TCGGCAAGTA TAGCAACGAT ACCGCCGGCC TG TTCCACCA CAATGGGGGC
```

FIG. 9B

| 550 | 560 | 570 | 580 | 590 | 600 |
|---|---|---|---|---|---|
| ACCGAT TTC T | CGACGACTGA | AAGCGGTATC | TACAAGAACC | TGTACGATCT | CGCGGATATC |
| 610 | 620 | 630 | 640 | 650 | 660 |
| AATCAGA ACA | ACAACACCAT | CGACTCGTAT | CTCAAGGAAT | CGATCCAGCT | GTGGCTGAAT |
| 670 | 680 | 690 | 700 | 710 | 720 |
| CTCGGAGTCG | ACGGGCATCCG | CTTCGACGCC | GTGAAGCATA | TGCCTCAGGG | CTGGCAGAAG |
| 730 | 740 | 750 | 760 | 770 | 780 |
| AGCTACG TCT | CGTCGATCTA | CAGCAGCGCC | AATCCGGTGT | TCACC TTCGG | TGAATGGTTC |
| 790 | 800 | 810 | 820 | 830 | 840 |
| CTCGGCCCCG | ACGAAAATGAC | CCAGGACAAC | ATCAACTTCG | CGAATCAGAG | CGGCATGCAC |
| 850 | 860 | 870 | 880 | 890 | 900 |
| CTGCTG GACT | TTGCGTTTGC | GCAGGAAATC | CGTGAAGTGT | TCCGGACAA | GTCGGAGACG |
| 910 | 920 | 930 | 940 | 950 | 960 |
| ATGACCGACC | TGAACTCGGT | GATCTCCAGC | ACCGGCTCCA | GCTATAA TTA | CATCAACAAC |
| 970 | 980 | 990 | 1000 | 1010 | 1020 |
| ATGG TTACGT | TCATCGACAA | CCATGACATG | GACCGCTTCC | AGCAAGCCGG | AGCGAGCACT |
| 1030 | 1040 | 1050 | 1060 | 1070 | 1080 |
| CGCCCGACCG | AGCAGGCTCT | TGCGGTAACG | CTGACTTCCC | GCGGCGTTCC | GGCAATCTAC |

FIG. 9C

```
     1090       1100        1110        1120        1130        1140
TACGGTACAG  AGCAA TATAT  GACCGGCAAC  GGCGACCCGA  ACAACCGCGG  CATGATGACC 1150       1160        1170        1180        1190        1200
GGCTTCGATA  CGAACAAGAC  AGCGTACAAA  GT GATCAAGG  CGCTGGCTCC  GCTTCGCAAG 1210       1220        1230        1240        1250        1260
TCCAACCCGG  CTCTCGCCTA  CGGCTCGACG  AC CCAGCGTT  GGGTGAACAG  CGACGTCTAC 1270       1280        1290        1300        1310        1320
GTAT ATGAAC  GCAAGTTCGG  AAGCAACGTA  GC T TTCGTTG  CCGTCAACCG  CAGCTCGACG 1330       1340        1350        1360        1370        1380
ACTGCCT ATC  CGATATCGGG  AGCGC TTACT  GC TCTGCCAA  ACGGAACGTA  TACCGACGTT 1390       1400        1410        1420        1430        1440
CTCGGGCGGCC TGC TTAATGG  CAATT CAATT  AC CGTTAACG  GCGGCACGGT  CAGCAA CTTT 1450       1460        1470        1480        1490        1500
ACACT TGCAG  CGGGGCGGTAC GGCAGTCTGG  CAGTACACGA  CGACGGAATC  CTCGCC GATT 1510       1520        1530        1540        1550        1560
ATCGGCAACG  TCGGCCCGAC  TATGGGCAAG  CCCGGCAACA  CCATCACGAT  CGACGGACGC 1570       1580        1590        1600        1610        1620
GGCTT CGGTA  CTACGAAGAA  CAAAGTT ACT  T TCGGTACGA  CAGCCGTTAC  CGGGCGGAAC
```

FIG. 9D

```
1630        1640        1650        1660        1670        1680
ATCGTGAGCT  GGGAAGATAC  CGAAATCAAG  GTCAAAG TTC CGAACGTGGC  CGCCGGCAAC 1690        1700        1710        1720        1730        1740
ACGGCCGTTA  CGGTAACGAA  CGCCGCCGGC  ACTACCAGCG  CAGCGTTCAA  CAACT T TAAC 1750        1760        1770        1780        1790        1800
GTACTGACTG  CCGA TCAGGT  CACTGTCCGC  TTCAAAGTCA  ACAATGCCAC  CACGGCCCTG 1810        1820        1830        1840        1850        1860
GGACAAAACG  TCTACCTGAC  CGGTAACGTC  GCCGAGCTTG  GCAACTGGAC  AGCCGCCAAC 1870        1880        1890        1900        1910        1920
GCAATCGGTC  CGATGTACAA  CCAGGTAGAA  GCCAGCTATC  CGAC TTGGTA  CT TCGACGTC 1930        1940        1950        1960        1970        1980
AGCGTTCCGG  CCAACACGGC  GCTGCAATTC  AA GTTCATCA  AAGTGAACGG  CT CGACAGTG 1990        2000        2010        2020        2030        2040
ACTTGGGAAG  GCGGCAACAA  CCACACCTTC  ACCTCGCCTT  CGAGCGGGCGT TGCGACCGTA 2050        2060
ACGGTCGATT  GGCAGAAC
```

FIG. 10

```
         10         20         30         40         50         60
A TGAAAAAGC AAGTCAAATG GTTGACGTCG GTGTCGATGT CCGTAGGGAT CGCACTCGGC
         70         80         90
GCGGCGCTGC CTGTATGGGC A
```

FIG. 11

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1> | Met | Lys | Lys | Gln | Val | Lys | Trp | Leu | Thr | Ser | Val | Ser | Met | Ser | Val |
| 16> | Gly | Ile | Ala | Leu | Gly | Ala | Ala | Leu | Pro | Val | Trp | Ala |  |  |  |

FIG. 12A

| | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1> | Ser | Pro | Asp | Thr | Ser | Val | Asn | Asn | Lys | Leu | Asn | Phe | Ser | Thr | Asp |
| 16> | Thr | Val | Tyr | Gln | Ile | Val | Thr | Asp | Arg | Phe | Val | Asp | Gly | Asn | Ser |
| 31> | Ala | Asn | Asn | Pro | Thr | Gly | Ala | Ala | Phe | Ser | Ser | Asp | His | Ser | Asn |
| 46> | Leu | Lys | Leu | Tyr | Phe | Gly | Gly | Asp | Trp | Gln | Gly | Ile | Thr | Asp | Phe |
| 61> | Ile | Asn | Asp | Gly | Tyr | Leu | Thr | Asp | Met | Gly | Ile | Thr | Ala | Leu | Asp |
| 76> | Ile | Ser | Gln | Pro | Val | Glu | Asn | Ile | Gly | Ala | Val | Ile | Asn | Tyr | Trp |
| 91> | Gly | Val | Asn | Asn | Thr | Ala | Tyr | His | Thr | Tyr | Trp | Pro | Arg | Asp | Ser |
| 106> | Lys | Lys | Thr | Asn | Ala | Ala | Phe | Gly | Ser | Phe | Thr | Asp | Phe | Ser | Phe |
| 121> | Leu | Ile | Ala | Ala | His | His | Ser | His | Asn | Ile | Lys | Val | Val | Met | Asn |
| 136> | Phe | Ala | Pro | Asn | Gly | Thr | Asn | Pro | Ala | Ser | Ser | Thr | Asp | Pro | Asp |
| 151> | Phe | Ala | Glu | Asn | Gly | Ala | Leu | Tyr | Asn | Asn | Gly | Thr | Leu | Leu | Ser |
| 166> | Lys | Tyr | Ser | Asn | Asp | Thr | Ala | Ser | Leu | Phe | His | His | Asn | Gly | Gly |
| 181> | Thr | Asp | Phe | Ser | Thr | Thr | Glu | Asn | Gly | Ile | Tyr | Lys | Asp | Leu | Tyr |
| 196> | Asp | Leu | Ala | Asp | Ile | Asn | Gln | Trp | Asn | Asn | Thr | Ile | Val | Ser | Tyr |
| 211> | Leu | Lys | Glu | Ser | Ile | Gln | Leu | His | Leu | Asn | Leu | Gly | Trp | Asp | Gly |
| 226> | Ile | Arg | Phe | Asp | Ala | Val | Lys | Ser | Met | Pro | Gln | Gly | Val | Gln | Lys |
| 241> | Ser | Tyr | Val | Ser | Ser | Ile | Tyr | Pro | Ser | Ala | Asn | Pro | Val | Ser | Thr |
| 256> | Phe | Gly | Glu | Trp | Phe | Leu | Gly | Pro | Asp | Glu | Met | Pro | Gln | _Phe_ | _Thr_ |
| 271> | Ile | Asn | Phe | Ala | Asn | Gln | Ser | Gly | Met | His | Leu | Leu | Asp | Asp | Asn |
| 286> | Phe | Ala | Gln | Glu | Asn | Arg | Glu | Val | Phe | Arg | Asp | Lys | Ser | Phe | Ala |
| 301> | Met | Thr | Asp | Leu | Asn | Met | Thr | Ile | Ser | Thr | Thr | Gly | Ser | Ser | Thr |
| 316> | Asn | Tyr | Ile | Asn | Asn | Tyr | Val | Thr | Phe | Ile | Asp | Asn | His | _Asp_ | _Met_ |
| 331> | Asp | Arg | Phe | Gln | Gln | Ala | Gly | Ser | Ser | Gly | Arg | Pro | Thr | Glu | Gln |
| 346> | Ala | Leu | Ala | Val | Thr | Leu | Thr | Thr | Arg | Ser | Val | Pro | Ala | _Ile_ | Tyr |
| 361> | Tyr | Gly | Thr | Glu | Gln | Tyr | Met | Asp | Gly | Asn | Gly | Asp | _Pro_ | _Asn_ | Asn |
| 376> | Arg | Gly | Met | Met | Thr | Gly | Phe | Asp | Thr | Asn | Lys | Thr | Ala | Tyr | Lys |

FIG. 12B

| | | | | | | | | | | | |
|---|---|---|---|---|---|---|---|---|---|---|---|
| 391> | Val | Ile | Lys | Ala | Leu | Ala | Pro | Leu | Arg | Lys | Ser | Asn | Pro | Ala | Leu |
| 406> | Ala | Tyr | Gly | Ser | Thr | Thr | Gln | Arg | Trp | Val | Asn | Ser | Asp | Val | Tyr |
| 421> | Val | Tyr | Glu | Arg | Lys | Phe | Gly | Ser | Asn | Val | Ala | Leu | Val | Ala | Val |
| 436> | Asn | Arg | Ser | Asn | Thr | Thr | Ala | Tyr | Pro | Ile | Ser | Gly | Ala | Leu | Thr |
| 451> | Ala | Leu | Pro | Ser | Gly | Thr | Thr | Thr | Thr | Asp | Val | Gly | Gly | Leu | Leu |
| 466> | Asn | Gly | Asn | Ala | Ile | Gly | Gly | Ile | Asn | Ala | Gly | Val | Tyr | Ser | Asn | Phe |
| 481> | Thr | Leu | Ser | Ala | Gly | Ile | Gly | Thr | Ala | Asp | Gly | Val | Thr | Thr | Thr | Thr |
| 496> | Glu | Ser | Pro | Thr | Ile | Thr | Phe | Gly | Val | Thr | Gly | Gln | Phe | Met | Gly | Lys |
| 511> | Pro | Gly | Asn | Val | Phe | Asp | Asp | Ile | Thr | Gly | Arg | Pro | Gly | Val | Gly | Thr |
| 526> | Lys | Asn | Lys | Ser | Thr | Ala | Thr | Ala | Ile | Thr | Ala | Val | Val | Thr | Ala | Asn |
| 541> | Ile | Val | Ser | Ala | Glu | Asn | Thr | Phe | Thr | Val | Lys | Thr | Val | Ala | Pro | Asn |
| 556> | Val | Ala | Ala | Arg | Asn | Ala | Phe | Asn | Asn | Val | Leu | Met | Leu | Ala | Ala | Gly |
| 571> | Thr | Thr | Ser | Tyr | Tyr | Leu | Phe | Asn | Asn | Val | Thr | Thr | Thr | Thr | Ala | Asp |
| 586> | Gln | Val | Thr | Asn | Ala | Ala | Pro | Met | Val | Thr | Glu | Leu | Gln | Gly | Val | Leu |
| 601> | Gly | Gln | Pro | Thr | Trp | Ile | Tyr | Phe | Ile | Asp | Val | Glu | Asn | Asn | Val | Asn |
| 616> | Trp | Thr | Gly | Gln | Lys | Trp | Phe | Lys | Tyr | His | Lys | Ser | Asn | Pro | Ala | Glu |
| 631> | Ala | Leu | Gly | Phe | Asn | Asn | Phe | Lys | Phe | Thr | Val | Asn | Val | Gly | Thr | Asn |
| 646> | Thr | Glu | Gly | Gly | Val | Gly | Ala | Asn | Asp | Trp | Thr | Phe | Gly | Ser | Ser | Val |
| 661> | Thr | Trp | Glu | Phe | Thr | Lys | Asn | His | Thr | Phe | Pro | Gln | Pro | Ser | Thr | Asn |
| 676> | Gly | Val | Ala | Val | Thr | Thr | Val | Val | Gln | Asn | Ser | Ser | Pro | Ser | Ser | Ser |

FIG. 12B

POLYPEPTIDE POSSESSING CYCLOMALTODEXTRIN GLUCANOTRANSFERASE ACTIVITY

CROSS-REFERENCE TO RELATED APPLICATIONS

This application is a continuation of application Ser. No. 07/438,933, filed Nov. 22, 1989, now abandoned which was a continuation of application Ser. No. 06/804,487, filed Dec. 4, 1985, now abandoned.

FIELD OF THE INVENTION

The present invention relates to a polypeptide, and particularly a polypeptide possessing cyclomaltodextrin glucanotransferase activity. The present invention also relates to DNA, microorganisms and processes related to the production of such polypeptide.

ABBREVIATIONS

Throughout the present specification and claims, amino acids, peptides, etc., are designated with abbreviations which are commonly used in the art. Examples of such abbreviations are as follows.

When optical isomers are possible, the abbreviations of amino acids mean L-isomers, unless specified otherwise.

DNA is the abbreviation of deoxyribonucleic acid; RNA ribonucleic acid; A, adenine; T, thymine; G, guanine; C, cytosine; dNTP, deoxynucleotide triphosphate; ddNTP, dideoxynucleotide triphosphate; dCTP, deoxycytidin triphosphate; SDS, sodium dodecyl sulfate; Ala, alanine; Arg, arginine; Asn, asparagine; Asp, aspartic acid; Cys, cysteine; Gln, glutamine; Glu, glutamic acid; Gly, glycine; His, histidine; Ile, isoleucine; Leu, leucine; Lys, lysine; Met, methionine; Phe, phenylalanine; Pro, proline; Ser, serine; Thr, threonine; Trp, tryptophan; Tyr, tyrosine; Val, valine; and CGTase, cyclomaltodextrin glucanotransferase.

The wording of "polypeptide" means "polypeptide possessing CGTase activity".

DESCRIPTION OF THE PRIOR ART

CGTase, or macerans, has been known for years as an enzyme produced by Bacillus macerans.

Recently, it was found that CGTase is produced by other microorganisms such as those of species Bacillus stearothermophilus and Bacillus circulans. The saccharide transfer activity of CGTase now has many industrial uses.

For example, cyclodextrins are produced by subjecting gelatinized starch to the action of CGTase, while glycosylsucrose production utilizes the saccharide transfer reaction from starch to sucrose which is effected by subjecting a mixture solution of liquefied starch and sucrose to CGTase.

Cyclodextrins are now expanding as a host for forming stable inclusion complexes with organic compounds which are volatile or susceptible to oxidation. Demand for glycosylsucrose is also expanding as a mildly-sweet low-cariogenic sweetener which is commercialized by Hayashibara Co., Ltd., Okayama, Japan, under the Registered Trademark of "Coupling Sugar".

In order to meet these demands, development of means to provide a constant CGTase supply is an urgent necessity. This requires determination of the amino acid sequence of the polypeptide that possesses CGTase activity.

Such amino acid sequence has, however, so far been unknown.

BRIEF DESCRIPTION OF THE ACCOMPANYING DRAWINGS

FIGS. 5(A-D) show the nucleotide sequence of the polypeptide gene derived from Bacillus stearothermophilus.

FIG. 6 shows the nucleotide sequence of the signal peptide gene located upstream of the 5'-terminal end of the polypeptide gene of FIG. 5.

FIG. 7 shows the amino acid sequence of the signal peptide of FIG. 6.

FIGS. 8(A-B) show the amino acid sequence of the polypeptide determined with reference to the sequence shown in FIG. 5.

FIGS. 9(A-D) show the nucleotide sequence of the polypeptide gene derived from Bacillus macerans.

FIG. 10 shows the sequence of the signal peptide located upstream of the 5'-site of the polypeptide of FIG. 9.

FIG. 11 shows the amino acid sequence of the signal peptide of FIGS. 10(A-B).

FIGS. 12(A-B) show the amino acid sequence of the polypeptide derived from Bacillus macerans.

SUMMARY OF THE INVENTION

Figure 1:
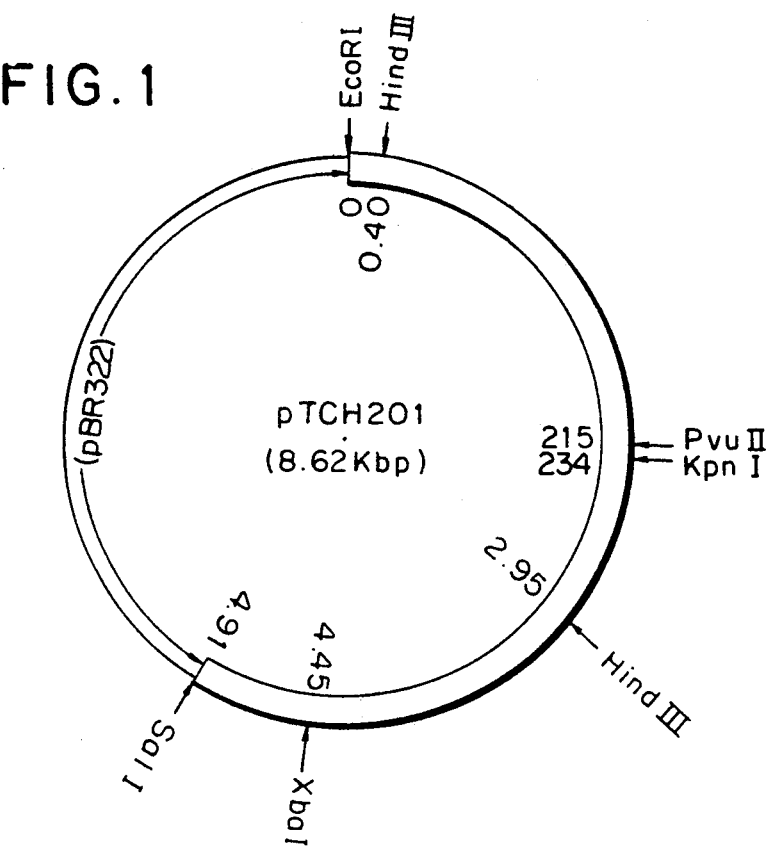
FIG. 1 shows the restriction map of recombinant DNA pTCH201, in particular that of the DNA fragment which carries the polypeptide gene derived from Bacillus stearothermophilus.

The present inventors carried out investigations to determine the amino acid sequence of CGTase polypeptide; to assure a wide polypeptide availability by recombinant gene technology; and also to improve polypeptide productivity.

As a result, the present inventors found that the CGTase polypeptide comprises one or more partial amino acid sequences selected from the group consisting of (a) Asn-Lys-Ile-Asn-Asp-Gly-Tyr-Leu-Thr,
(b) Pro-Val-Phe-Thr-Phe-Gly-Glu-Trp-Phe-Leu,
(c) Val-Thr-Phe-Ile-Asp-Asn-His-Asp-Met-Asp-Arg-Phe,
(d) Ile-Tyr-Tyr-Gly-Thr-Glu-Gln-Tyr-Met-Thr-Gly-Asn-Gly-Asp-Pro-Asn-Asn-Arg, and
(e) Asn-Pro-Ala-Leu-Ala-Tyr-Gly, and that, more particularly, these partial amino acids sequences (a), (b), (c), (d) and (e) are located in order of nearness to the N-terminal end of the polypeptide.

The polypeptide is characterized by the facts that it forms cyclodextrin from soluble starch; that it shows a molecular weight of 70,000±10,000 daltons on SDS-polyacrylamide electrophoresis; and that it has a specific activity of 200±30 units/mg protein.

The present inventors also found that polypeptides derived from *Bacillus stearothermophilus* and *Bacillus macerans* have the amino acid sequences as shown in FIGS. 8 and 12, respectively. Both amino acid sequences will be discussed hereafter.

In addition, the present inventors determined the amino acid sequences of the signal peptides which regulate polypeptide secretion from producer microorganisms.

The present invention and features thereof will hereinafter be explained.

DESCRIPTION OF THE PREFERRED EMBODIMENTS

In the present invention, the amino acid sequence of the CGTase polypeptide is determined by cloning the polypeptide gene from a CGTase producer microorganism and sequencing the polypeptide gene.

The amino acid sequence containing N-terminal end is determined by analyzing a highly-purified polypeptide with a gas-phase protein sequencer.

Cloning of the polypeptide gene

In the present invention, a DNA fragment, obtained by separating DNA from a donor microorganism capable of producing the polypeptide and digesting the DNA, for example with ultrasound or restriction enzymes, and a vector fragment, obtained by cleaving a vector in the same way, are ligated, for example with DNA ligase, to obtain a recombinant DNA carrying the polypeptide gene.

The donor microorganism is chosen from bacteria which produce the polypeptide. Examples of such bacteria are those of genus Bacillus such as *Bacillus macerans, Bacillus megaterium, Bacillus circulans, Bacillus polymyxa,* and *Bacillus stearothermophilus,* and those of genus Klebsiella such as *Klebsiella pneumoniae,* as described, for example, in Japan Patent Kokai No. 20,373/72, Japan Patent Kokai No. 63,189/75, Japan Patent Kokai No. 88,290/75, and Hans Bender, *Archives of Microbiology,* Vol.111, pp.271-282 (1977).

Recombinant microorganisms in which polypeptide producibility has been introduced by genetic engineering techniques can also be used as the donor microorganism.

The DNA of the donor microorganism can be prepared by culturing the donor microorganism, for example with a liquid culture medium for about 1-3 days under aeration-agitation conditions, centrifugally collecting the microorganism from the culture, and lysing the microorganism. Examples of bacteriolytic procedures are cytohydrolysis using lysozyme or β-glucanase, and ultrasonic treatment.

Other enzymes, such as protease, and/or surface active agents, such as sodium lauryl sulfate, can be used in combination, if necessary. Of course, freezing-thawing treatment can be carried out, if necessary.

In order to isolate DNA from the resultant lysate, two or more conventional procedures, such as phenol extraction, protein removal, protease treatment, ribonuclease treatment, alcohol sedimentation, and centrifugation, are combined.

Although DNA ligation can be effected by treating DNA- and vector-fragments, for example with ultrasound or restriction enzymes, it is desirable to use restriction enzymes, particularly those acting specifically on a prescribed nucleotide sequence, for smooth ligation. Specifically suited are Type II restriction enzymes, for example, EcoRI, HindIII, BamHI, SalI, SlaI, XmaI, MboI, XbaI, SacI, PstI, etc.

Bacteriophages and plasmids which autonomically proliferate in the host microorganism are suitable for vectors.

When a microorganism of species *Escherichia coli* is used as the host, bacteriophages such as λgt·λC and λgt·λB are employable, while ρ11, ψ1 and ψ105 are usable when a microorganism of species *Bacillus subtilis* is used as the host.

As regards plasmids, when a microorganism of species *Escherichia coli* is used as the host, plasmids such as pBR322 and pBR325 are employable, while pUB110, pTZ4 (pTP4) and pC194 are usable for a host microorganism of species *Bacillus subtilis.* Plasmids which autonomically proliferate in two or more different host microorganisms, for example, pHV14, TRp7, YEp7 and pBS7, can be used as the vector. These vectors are cleaved with the same types of restriction enzymes as used in DNA digestion to obtain a vector fragment.

DNA- and vector-fragments are ligated with conventional procedures using DNA ligase. For example, DNA- and vector-fragments are first annealed, then subjected in vitro to the action of a suitable DNA ligase to obtain a recombinant DNA. If necessary, such recombinant DNA can be prepared by introducing the annealed fragments into the host microorganism to subject them to in vivo DNA ligase.

The host microorganisms usable in the invention are those in which recombinant DNA autonomically and consistently proliferates to express its characteristics. Specifically, microorganisms which are not capable of producing α-amylase (EC 3.2.1.1) are preferably used because the use of such microorganisms facilitates isolation and purification of the secreted polypeptide.

The recombinant DNA can be introduced into the host microorganism with any conventional procedure. For example, when the host microorganism belongs to the species *Escherichia coli,* introduction of recombinant DNA is effected in the presence of calcium ion, while the competent cell- and protoplast-methods are employed when a host microorganism of genus Bacillus is used.

The recombinant microorganism in which recombinant DNA has been introduced is selected by collecting clones which grow on plate culture containing starch to convert the starch into cyclodextrin.

The present inventors found that the recombinant DNA carrying the polypeptide gene cloned in this way can be easily introduced, after isolation from the recombinant microorganism, into a different host microorganism. It was also found that a DNA fragment carrying the polypeptide gene, obtained by digesting a recombinant DNA carrying the gene with restriction enzymes, can be easily ligated with a vector fragment which has been obtained in the same manner.

Furthermore, the present inventors found that the polypeptide gene in the recombinant DNA obtained according to the present invention is cleaved by restriction enzyme PvuII, purchased from Toyobo Co., Ltd., Osaka, Japan, to lose the ability of expressing the polypeptide gene because the recombinant DNA has a PvuII restriction cleavage site.

Sequence of the polypeptide gene

The polypeptide gene is sequenced by the chain-terminator method as described in Gene, Vol.9, pp. 259-268(1982).

This method contains the step of inserting a cloned DNA fragment carrying the polypeptide gene into the insertion site of a suitable plasmid such as pUC18 using restriction enzymes. The obtained recombinant plasmid is introduced by transformation into a suitable *Escherichia coli* strain such as *Escherichia coli* JM83, followed by selection of the recombinant microorganism that contains the plasmid.

The recombinant plasmid is prepared from the proliferated recombinant microorganism.

The obtained recombinant plasmid is annealed together with a synthetic primer, and the Klenow fragment is then allowed to act on the mixture to extend the primer, as well as to form the complementary DNA.

Thereafter, the mixture is subjected sequentially to polyacrylamide-electrophoresis and radioautography, followed by sequencing of the polypeptide gene.

The signal polypeptide which regulates polypeptide secretion from the cell is sequenced in the same manner.

Amino acid sequence of the polypeptide

The amino acid sequence of the polypeptide is determined from the DNA sequence of the polypeptide gene.

The amino acid sequence of the signal peptide is determined in the same manner.

N-terminal amino acid sequence of the polypeptide

A polypeptide producer microorganism of genus Bacillus is cultured with a nutrient culture medium to produce the polypeptide. The supernatant, centrifugally obtained from the culture, is purified by ammonium sulfate fractionation, ion exchange chromatography and high-performance liquid chromatography to obtain a high-purity polypeptide specimen. The specimen is then degraded with a gas-phase protein sequencer in accordance with the method described in *Journal of Biological Chemistry*, Vol. 256, pp. 7990–7997 (1981), and isolated with high-performance liquid chromatography, followed by determination of the partial amino acid sequence of the N terminal end.

Preparation of polypeptide with recombinant microorganism

The present inventors found that a large amount of polypeptide can be consistently produced by culturing a recombinant microorganism with a nutrient culture medium.

To the nutrient culture medium is incorporated, for example, a carbon source, a nitrogen source, minerals, and, if necessary, small amounts of organic nutrients such as amino acids and vitamins.

Starch, partial starch hydrolysate, and saccharides such as glucose, fructose and sucrose are suitable for the carbon source. Inorganic nitrogen sources such as ammonia gas, ammonia water, ammonium salts and nitrates; organic nitrogen sources such as peptone, yeast extract, and defatted soybean, corn steep liquor and meat extract are suitable for the nitrogen source.

The recombinant microorganism is cultured with a nutrient culture medium for about 1–4 days under aeration-agitation conditions to accumulate polypeptide while keeping the culture medium, for example, at pH 4°–10° and 25°–65° C.

Although the polypeptide in the culture may be used intact, generally the culture is separated into polypeptide solution and cells with conventional procedures such as filtration and centrifugation, prior to its use.

When the polypeptide is present in the cells, the cells are first treated with ultrasound, surface active agent and/or cytohydrolysis, then with filtration and centrifugation to separate a solution containing the polypeptide.

The solution containing the polypeptide thus obtained is purified, for example by combination of concentration in vacuo, concentration using a membrane filter, salting-out using ammonium sulfate or sodium sulfate, fractional sedimentation using methanol, ethanol or acetone, to obtain a highly-purified polypeptide specimen which is advantageously usable as industrial polypeptide material.

To further improve the quality of the polypeptide, the amino acid sequence of the polypeptide may be partially substituted, removed, added, or modified in such a manner that the polypeptide does not lose its CGTase activity prior to its use.

One unit of CGTase activity is defined as the amount of polypeptide that diminishes completely the iodine-coloration of 15 mg soluble starch at 40° C. over a period of 10 minutes under the following reaction conditions: To 5 ml of 0.3 w/w % soluble starch solution containing 0.02 M acetate buffer (pH 5.5) and $2 \times 10^{-3}$ M calcium chloride is added 0.2 ml of a diluted enzyme solution, and the mixture is incubated at 40° C. for 10 minutes. Thereafter, 0.5 ml of the reaction mixture is sampled and 15 ml of 0.02 N aqueous sulfuric acid solution is added to suspend the enzymatic reaction. To the reaction mixture 0.2 ml of 0.1 N $I_2$-KI solution is added to effect coloration, and its absorbance at a wavelength of 660 nm is determined.

Deposition of recombinant microorganisms

Recombinant microorganisms *Escherichia coli* TCH201, *Escherichia coli* MAH2, *Bacillus subtilis* MAU210, and *Bacillus subtilis* TCU211 have been deposited under the accession numbers of FERM BP-2109, BP-2110, BP-2111, and BP-2112, respectively, at the Fermentation Research Institute, Agency of Industrial Science and Technology, 1-3, Higashi 1 chome, Yatabemachi, Tsukuba-gun, Ibaraki-ken, Japan.

Several embodiments according to the present invention are disclosed in the following examples:

EXAMPLE 1

Cloning of *Bacillus stearothermophilus* polypeptide gene into *Escherichia coli*

Preparation of chromosome DNA carrying the heat-resistant polypeptide gene of *Bacillus stearothermophilus*

The chromosome DNA carrying the heat-resistant-polypeptide gene of *Bacillus stearothermophilus* was prepared in accordance with the method described by Saito and Miura, *Biochimica et Biophisica Acta*, Vol. 72, pp.619–629 (1963). A seed culture of *Bacillus stearothermophilus* FERM-P No. 2225 was cultured with brain heart infusion medium at 50° C. overnight under vigorous shaking conditions. The cells, centrifugally collected from the culture, were suspended with TES buffer (pH 8.0) containing Tris-aminomethane, hydrochloric acid, EDTA and sodium chloride, mixed with 2 mg/ml of lysozyme, and incubated at 37° C. for 30 minutes. The incubated mixture was frozen, allowed to stand at −20° C. overnight, mixed with TSS buffer (pH 9.0) containing Tris-aminomethane, hydrochloric acid, sodium lauryl sulfate and sodium chloride, heated to 60° C., mixed with a mixture of TES buffer (pH 7.5) and phenol (1:4 by volume), cooled in ice-chilled water, and centrifuged to obtain a supernatant. To the supernatant was added two volumes of cold ethanol to recover a crude chromosomal DNA which was then dissolved in SSC buffer (pH 7.1) containing sodium chloride and trisodium citrate; thereafter, the mixture was subjected to both "RNase A", a ribonuclease commercialized by Sigma Chemical Co., Mo., USA, and "Pronase E", a protease commercialized by Kaken Pharmaceutical Co., Ltd., Tokyo, Japan, mixed with a fresh preparation of TES buffer and phenol mixture, cooled, centrifuged, and mixed with two volumes of cold ethanol to recover a purified chromosomal DNA. The chromosomal DNA was dissolved in a buffer (pH 7.5) containing Tris-aminomethane, hydrochloric acid and EDTA, and stored at −20° C.

EXAMPLE 1-(2)

Preparation of plasmid pBR322

Plasmid pBR322 (ATCC 37013) was isolated from *Escherichia coli* in accordance with the method described by J. Meyer et al. in *Journal of Bacteriology*, Vol. 127, pp. 1524–1537 (1976).

(EXAMPLE 1-(3)

Preparation of recombinant DNA carrying polypeptide gene

The purified chromosomal DNA carrying the heat-resistant-polypeptide gene, prepared in Example 1-(1), was partially digested with restriction enzyme MboI, purchased from Nippon Gene Co., Ltd., Toyama, Japan, to give DNA fragments of 1–20 kbp. Separately, the pBR322 specimen, prepared in Example 1-(2), was completely cleaved with restriction enzyme BamHI, purchased from Nippon Gene Co., Ltd., and the cleaved product was subjected to *Escherichia coli* alkaline phosphatase, purchased from Takara Shuzo Co., Ltd., Kyoto, Japan, to prevent self-ligation of the plasmid fragment as well as to dephosphorize the 5′-terminal end of the fragment.

Both fragments were then ligated by subjecting them to $T_4$ DNA ligase, purchased from Nippon Gene Co., Ltd., at 4° C. overnight to obtain a recombinant DNA.

EXAMPLE 1-(4)

Introduction of recombinant DNA into *Escherichia coli*

*Escherichia coli* HB101 (ATCC 33694), a strain incapable of producing amylase, was used as the host.

The microorganism was cultured with L-broth at 37° C. for 4 hours, and the cell, centrifugally collected from the culture, was suspended with 10 mM acetate buffer (pH 5.6) containing 50 mM manganese chloride, centrifugally collected again, resuspended with 10 mM acetate buffer (pH 5.6) containing 125 mM manganese chloride, mixed with the recombinant DNA prepared in Example 1-(3), and allowed to stand in an ice chilled water bath for 30 minutes. The mixture was then warmed to 37° C., mixed with L-broth, spread on L-broth agar plate medium containing 50 μg/ml of ampicillin and 2 mg/ml starch, and incubated at 37° C. for 24 hours to form colonies.

The colonies which had degraded the starch into cyclodextrin were selected by the iodine-coloration method. Thus, the microorganisms in which the recombinant DNA carrying polypeptide gene had been introduced were selected. A recombinant microorganism was then proliferated, and the recombinant DNA was extracted from the proliferated microorganism by the plasmid preparation method in Example 1-(2), subjected to restriction enzymes to determine the restriction cleavage sites, and completely digested with restriction enzyme EcoRI purchased from Nippon Gene Co., Ltd.

The digested product was subjected to $T_4$ DNA ligase similarly as in Example 1-(3) to obtain a recombinant DNA, followed by selection of a recombinant microorganism in accordance with the method in Example 1-(4). The recombinant microorganism contained a recombinant DNA of a relatively small-size that carries no polypeptide gene.

The recombinant DNA and plasmid pBR322 were then completely digested with restriction enzyme SalI, purchased from Nippon Gene Co., Ltd., and treated similarly as in the case of EcoRI to select recombinant microorganisms containing a recombinant DNA of a much smaller-size that carries the polypeptide gene.

One of these microorganisms and its recombinant DNA were named as "*Escherichia coli* TCH201 (FERM BP-2109)" and "pTCH201".

The restriction map of recombinant DNA pTCH201, in particular that of the DNA fragment derived from *Bacillus stearothermophilus* microorganism, is as shown in FIG. 1.

FIG. 1 clearly shows that the DNA fragment carrying the polypeptide gene derived from *Bacillus stearothermophilus* microorganism is cleaved by either restriction enzyme PvuII purchased from Toyobo Co., Ltd., KpnI, HindIII purchased from Nippon Gene Co., Ltd., or XbaI purchased from Takara Shuzo Co., Ltd, but not by EcoRI, BamHI, PstI, XhoI, BglII or AccI, all purchased from Nippon Gene Co., Ltd.

EXAMPLE 2

Cloning of polypeptide gene of *Bacillus stearothermophilus* into *Bacillus subtilis*

EXAMPLE 2-(1)

Preparation of recombinant DNA pTCH201

Recombinant DNA pTCH201 was isolated from *Escherichia coli* TCH201 (FERM BP-2109) in accordance with the method in Example 1-(2).

EXAMPLE 2-(2)

Preparation of plasmid pUB110

Plasmid pUB110 (ATCC 37015) was isolated from *Bacillus subtilis* in accordance with the method described by Gryczan et al. in *Journal of Bacteriology*, Vol.134, pp. 318–329 (1978).

EXAMPLE 2-(3)

Preparation of recombinant DNA carrying polypeptide gene

The recombinant DNA pTCH201 carrying the heat-resistant-polypeptide gene prepared in Example 2-(1), was completely digested by subjecting it simultaneously to restriction enzymes EcoRI and XbaI.

Separately, the plasmid pUB110 specimen, prepared in Example 2-(2), was completely cleaved by subjecting it to restriction enzymes EcoRI and XbaI in the same manner.

The resultant fragments were subjected to $T_4$ DNA ligase similarly as in Example 1-(3) to obtain a recombinant DNA.

EXAMPLE 2-(4)

Introduction of recombinant DNA into *Bacillus subtilis*

In this Example, *Bacillus subtilis* 715A, a strain incapable of producing amylase, was used as the host. The microorganism was cultured with brain heart infusion medium at 28° C. for 5 hours, and the cell, centrifugally collected from the culture, was then prepared into protoplast suspension in accordance with the method described by Schaeffer et al. in *Proceedings of the National Academy of Sciences of the USA*, Vol.73, pp.2151–2155 (1976).

To the suspension was added the recombinant DNA, prepared in Example 2-(3), and the mixture was then treated in accordance with the method described by Sekiguchi et al. in *Agricultural and Biological Chemistry*, Vol.46, pp.1617–1621 (1982) to effect transformation, spread on HCP medium containing 250 μg/ml of kanamycin and 10 mg/ml of starch, and incubated at 28° C. for 72 hours to form colonies.

From these colonies, recombinant microorganisms in which the recombinant DNA carrying the heat-resistant-polypeptide gene had been introduced were selected by the method in Example 1-(4). One of these microorganisms and its recombinant DNA were named as "*Bacillus subtilis* TCU211 (FERM BP2-2112)" and "pTCU211", respectively.

Figure 2:
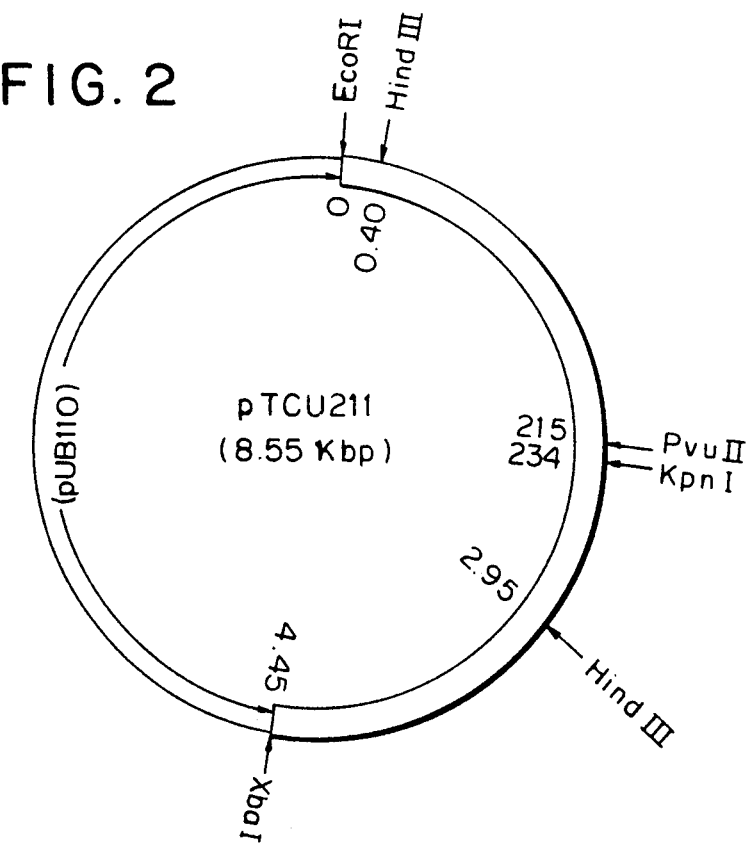
FIG. 2 shows the restriction map of recombinant DNA pTCU211, in particular that of the DNA fragment which carries the polypeptide gene derived from Bacillus stearothermophilus.

The restriction map of recombinant DNA pTCU211, in particular that of the DNA fragment derived from *Bacillus stearothermophilus* microorganism, is as shown in FIG. 2. FIG. 2 clearly shows that the DNA fragment carrying the polypeptide gene derived from *Bacillus stearothermophilus* microorganism is cleaved by either restriction enzyme PvuII, KpnI or HindIII, but not by EcoRI, BamHI, PstI, XhoI, BglII, AccI or XbaI.

EXAMPLE 3

N-terminal amino acid sequence of *Bacillus stearothermophilus* polypeptide

EXAMPLE 3-(1)

Preparation of polypeptide

*Bacillus stearothermophilus* FERM-P No.2225 was cultured with a liquid culture medium by the method in Example 5 to produce polypeptide. The supernatant, centrifugally obtained from the culture, was salted out with ammonium sulfate to obtain a polypeptide fraction which was then purified by column chromatography using "DEAE Toyopearl 650", an anion exchanger commercialized by Toyo Soda Manufacturing Co., Ltd., Tokyo, Japan, and chromatofocusing using "Mono P", a product of Pharmacia Fine Chemicals AB, Uppsala, Sweden, to obtain a highly-purified polypeptide specimen.

On SDS-polyacrylamide electrophoresis in accordance with the method described by K. Weber and M. Osborn in *Journal of Biological Chemistry*, Vol. 244, page 4406 (1969), the polypeptide specimen showed a molecular weight of 70,000±10,000 daltons.

The specific activity of the polypeptide specimen was 200±30 units/mg protein.

EXAMPLE 3-(2)

N-terminal amino acid sequence of the polypeptide

A polypeptide specimen, prepared by the method in Example 3-(1), was fed to "Model 470A", a gas-phase protein sequencer, a product of Applied Biosystems Inc., Calif., USA, and then analyzed with high-performance liquid chromatography to determine the N-terminal partial amino acid sequence.

The partial amino acid sequence was Ala-Gly-Asn-Leu-Asn-Lys-Val-Asn-Phe-Thr.

EXAMPLE 4

Sequence of polypeptide gene derived from *Bacillus stearothermophilus* and amino acid sequence of polypeptide

EXAMPLE 4-(1)

Preparation of plasmid pUC18

Plasmid pUC18 was prepared in accordance with the method in Example 1-(2) from *Escherichia coli* JM83 (ATCC 35607) in which the plasmid had been introduced.

EXAMPLE 4-(2)

Preparation of recombinant DNA carrying polypeptide gene

The recombinant DNA was prepared by the method in Example 1-(3).

A fragment, obtained by digesting a fragment carrying the polypeptide gene, prepared by the method in Example 2-(3), with restriction enzymes, and a plasmid fragment, obtained by cleaving a pUC18 specimen, prepared by the method in Example 4-(1), in the same manner, were subjected to $T_4$ DNA ligase to obtain a recombinant DNA.

EXAMPLE 4-(3)

Introduction of recombinant DNA into *Escherichia coli*

In this example, *Escherichia coli* JM83 was used as the host.

The recombinant DNA was introduced into this microorganism in accordance with the method in Example 1-(4) to transform the microorganism.

The recombinant microorganisms were inoculated to a culture medium containing 5-bromo-4-chloro-3-indoyl-β-galactoside (Xgal), and the microorganism forming colorless plaque was selected.

EXAMPLE 4-(4)

Preparation of recombinant DNA from recombinant microorganism

The recombinant microorganism was cultured on L-broth containing 50 μg/ml of ampicillin, and the obtained cells were then treated with the alkaline mini-preparation method to obtain a recombinant DNA.

EXAMPLE 4-(5)

Sequence of recombinant DNA

The recombinant DNA was sequenced by the dideoxy chain terminator method.

The recombinant DNA, prepared in Example 4-(4), and a synthetic primer composed of 17 bases were mixed, annealed at 60° C. for 20 minutes, mixed with dNTP, ddNTP, ($\alpha$-$^{32}$P) dCTP and Klenow fragment, and reacted at 37° C. for 30 minutes to extend the primer towards the 3' site from the 5' site. Thus, the complementary DNA was obtained. To the complementary DNA was added an excessive amount of dNTP, and the mixture was reacted at 37° C. for 30 minutes, followed by addition of a formamide solution of dye mixture to suspend the reaction. The reaction mixture was boiled for 3 minutes, and electrophoresed on 6% polyacrylamide gel at about 25 mA (about 2,000 volts) to separate the extended complementary DNA. After completion of the electrophoresis, the gel was fixed and dehydrated.

The dehydrated gel was then autographed, and the polypeptide gene was determined by analyzing the base bands on the radioautogram.

activity, while the cells were ultrasonically broken, prior to determination of their CGTase activity per culture. The results are as shown in Table 1.

TABLE 1

| Microorganism | CGTase activity (units/ml) | | | |
|---|---|---|---|---|
| | Supernatant | Cell | Total | |
| *Escherichia coli* TCH201 (FERM BP-2109) | 0.8 | 13.5 | 14.3 | Present invention |
| *Bacillus subtilis* TCU211 (FERM BP-2110) | 46.7 | 20.5 | 67.2 | Present invention |
| *Escherichi coli* HB101 | 0 | 0 | 0 | Control |
| *Bacillus subtilis* 715A | 0 | 0 | 0 | Control |
| *Bacillus stearothermophilus* FERM-P No. 2225 | 8.5 | 0.3 | 8.8 | Control |

The results are as shown in FIG. 5.

The signal peptide gene located upstream of the 5'-terminal end of the polypeptide gene was sequenced in the same manner.

The results are as shown in FIG. 6.

EXAMPLE 4-(6)

Amino acid sequence of the polypeptide

The amino acid sequence of the polypeptide was determined with reference to the sequence as shown in FIG. 5, and the results are as shown in FIG. 8.

The amino acid sequence of the signal peptide was determined in the same manner, and the results are as shown in FIG. 7.

This evidence confirms that the polypeptide derived from *Bacillus stearothermophilus* has the amino acid sequence as shown in FIG. 8.

EXAMPLE 5

Preparation of polypeptide with recombinant microorganism

Polypeptides were prepared with recombinant microorganisms *Escherichia coli* TCH201 (FERM BP-2109) and *Bacillus subtilis* TCU211 (FERM BP-2112) both in which recombinant DNA carrying the heat-resistant-polypeptide gene derived from *Bacillus stearothermophilus* had been introduced.

The polypeptide productivities of these recombinant microorganisms were compared with those of the host microorganisms without the recombinant plasmid and the donor *Bacillus stearothermophilus* microorganism in relation to their CGTase activity. A liquid culture medium consisting of 1.0 w/v % corn steep liquor, 0.1 w/v % ammonium sulfate, 1.0 w/v % calcium carbonate, 1 w/v % starch and water was adjusted to pH 7.2, sterilized by heating at 120° C. for 20 minutes, and cooled. In the case of *Escherichia coli* TCH201, the liquid culture medium was mixed with 50 μg/ml of ampicillin and the microorganism was inoculated to the liquid culture medium. *Escherichia coli* HB101 was inoculated to the liquid culture medium without addition of antibiotic. In each case, the microorganism was cultured at 37° C. for 48 hours under vigorous shaking conditions.

Separately, *Bacillus subtilis* TCU211 was inoculated to the liquid culture medium additionally containing 5 μg/ml of kanamycin, while *Bacillus subtilis* 715A was inoculated to the liquid culture medium without addition of antibiotic. In each case, the microorganism was cultured at 28° C. for 72 hours.

*Bacillus stearothermophilus* FERM-P No. 2225 was cultured with the liquid culture medium at 50° C. for 48 hours without addition of antibiotic. After separation of each culture into supernatant and cells by centrifugation, the supernatant was assayed intact for CGTase activity, while the cells were ultrasonically broken, prior to determination of their CGTase activity per culture. The results are as shown in Table 1.

This evidence clearly shows that the recombinant microorganisms are advantageously usable in industrial-scale production of polypeptide because these microorganisms possess an improved polypeptide productivity.

The supernatants were salted out with ammonium sulfate at a saturation degree of 0.6 to obtain crude polypeptide specimens. After studying these polypeptide specimens on their enzymatic properties, such as saccharide transfer form starch to sucrose, cyclodextrin production from starch, ratio of α, β- and λ-cyclodextrins, optimum temperature, optimum pH, stable temperature range and stable pH range, the properties of the polypeptide produced by the recombinant microorganism were in good accordance with those of the polypeptide produced by the donor *Bacillus stearothermophilus* microorganism.

EXAMPLE 6

Cloning of *Bacillus macerans* polypeptide gene into *Escherichia coli*

EXAMPLE 6-(1)

Preparation of chromosome DNA carrying *Bacillus macerans* polypeptide gene

The polypeptide gene was prepared in accordance with the method in Example 1-(1), except that *Bacillus macerans* 17A was cultured at 28° C.

EXAMPLE 6-(2)

Preparation of recombinant DNA carrying polypeptide gene

The chromosomal DNA carrying the polypeptide gene derived from *Bacillus macerans*, prepared in Example 6-(1), was partially digested similarly as in Example 1-(3) with restriction enzyme HindIII, purchased from Nippon Gene Co., Ltd.

Separately, a plasmid pBR322 specimen, prepared by the method in Example 1-(2), was completely cleaved with restriction enzyme HindIII, and the 5'-terminal end of the cleaved product was dephosphorized by the method in Example 1 (3). The fragments thus obtained were ligated in accordance with the method in Example 1-(3) to obtain a recombinant DNA.

EXAMPLE 6-(3)

Introduction of recombinant DNA into *Escherichia coli*

The recombinant microorganism in which recombinant DNA had been introduced was cloned in accordance with the method in Example 1-(4) using *Escherichia coli* HB101 (ATCC 33694), a strain incapable of producing amylase, as the host. Thereafter, the recombinant DNA was isolated from the microorganism, subjected to restriction enzymes to determine the restriction cleavage sites, and partially digested with restriction enzyme Sau3AI commercialized by Nippon Gene Co., Ltd.

Separately, a plasmid pBR322 specimen, obtained by the method in Example 1-(2), was completely cleaved with restriction enzyme BamHI. and the 5'-terminal end of the resultant product was dephosphorized similarly as in Example 1-(3). The obtained fragments were ligated with T4 DNA ligase to obtain a recombinant DNA, followed by selecting recombinant microorganisms in accordance with the method in Example 1-(4). The recombinant microorganisms contained a recombinant DNA of a relatively small-size that carries the polypeptide gene.

One of these recombinant microorganisms and its recombinant DNA were named as "*Escherichia coli* MAH2 (FERM BP-2110)" and "pMAH2" respectively.

Figure 3:
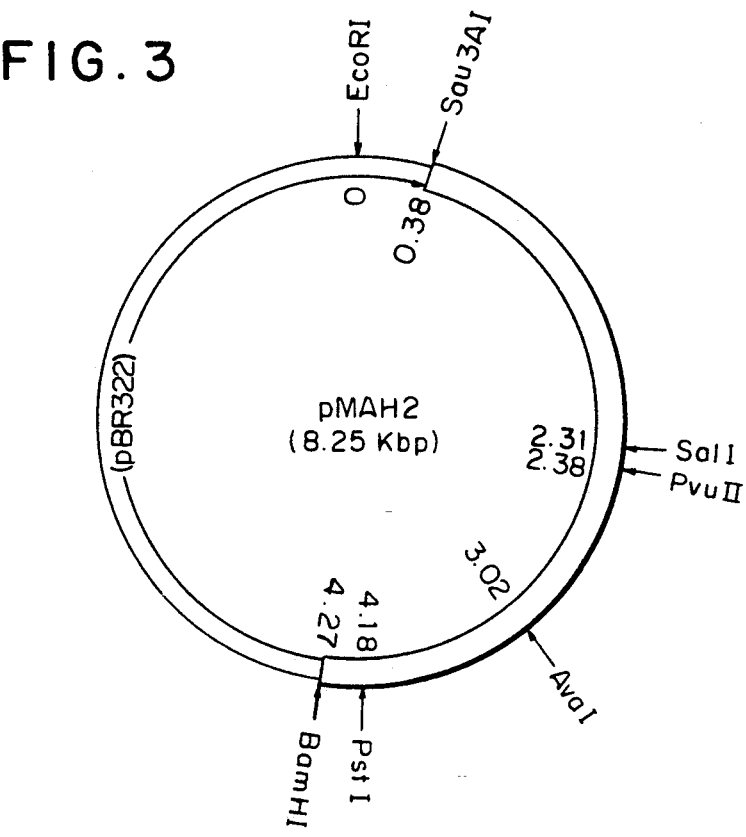
FIG. 3 shows the restriction map of recombinant DNA pMAH2, in particular that of the DNA fragment which carries the polypeptide gene derived from Bacillus macerans.

The restriction map of recombinant DNA pMAH2, in particular that of the DNA fragment that carries the polypeptide gene derived from *Bacillus macerans*, is as shown in FIG. 3.

FIG. 3 shows that the DNA fragment carrying the polypeptide gene derived from *Bacillus macerans* is cleaved by either restriction enzyme PvuII, SalI, AvaI commercialized by Nippon Gene Co., Ltd., or PstI commercialized by Nippon Gene Co., Ltd., but not by EcoRI, HindIII, KcnI, BamHI, XbaI, XhoI or SmaI.

EXAMPLE 7

Cloning of *Bacillus macerans* polypeptide oene into *Bacillus subtilis*

EXAMPLE 7-(1)

Preparation of recombinant DNA pMAH2

The recombinant DNA pMAH2 was isolated from *Escherichia coli* MAH2 (FERM BP-2110) in accordance with the method in Example 1-(2).

EXAMPLE 7-(2)

Preparation of recombinant DNA carrying the polypeptide gene

The recombinant DNA pMAH2 specimen carrying the polypeptide gene, prepared in Example 7-(1), was completely digested by subjecting it simultaneously to restriction enzymes EcoRI and BamHI.

The fragments thus obtained were subjected to T4 DNA ligase similarly as in Example 1-(3) to obtain a recombinant DNA.

EXAMPLE 7-(3)

Introduction of recombinant DNA into *Bacillus subtilis*

Recombinant microorganisms in which recombinant DNA carrying the polypeptide gene derived from *Bacillus macerans* had been introduced were cloned in accordance with the method in Example 2-(4) using *Bacillus subtilis* 715A, a strain incapable of producing amylase.

Figure 4:
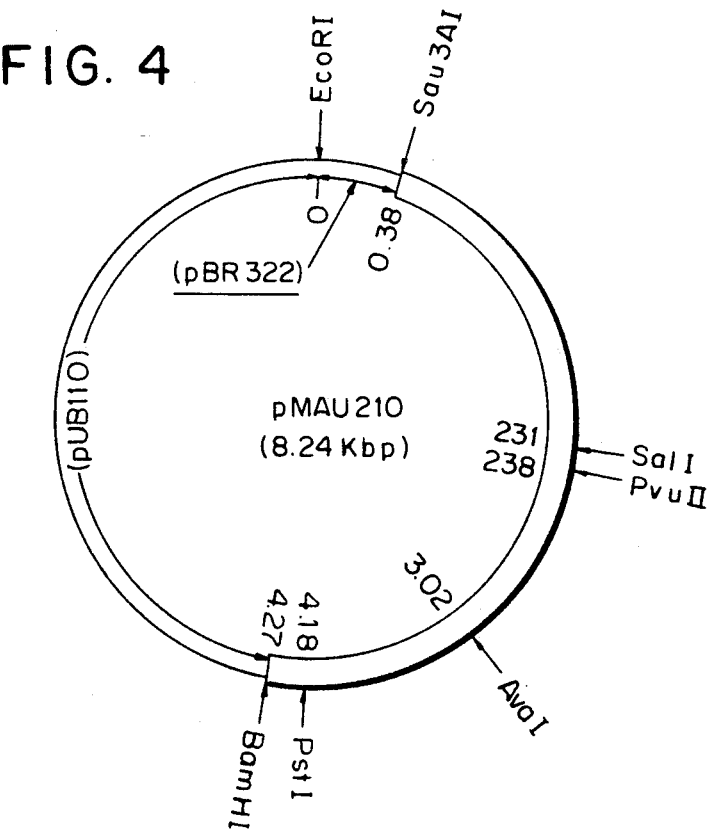
FIG. 4 shows the restriction map of recombinant DNA pMAU210, in particular that of the DNA fragment which carries the polypeptide gene derived from Bacillus macerans.

One of the recombinant microorganisms and its recombinant DNA were named as "Bacillus subtilis MAU210 (FERM "BP-2111)" and "pMAU210" respectively. The restriction map of recombinant DNA pMAU210, in particular that of the DNA fragment that carries the polypeptide gene derived from Bacillus macerans, was as shown in FIG. 4. FIG. 4 shows that this DNA fragment carrying the polypeptide gene derived from *Bacillus macerans*, is cleaved by either restriction enzyme PvuII, SalI, AvaI or PstI, but not by EcoRI, HindIII, KpnI, BamHI, XbaI, XhoI or SmaI.

EXAMPLE 8

N-terminal amino acid sequence of the polypeptide derived from *Bacillus macerans*

EXAMPLE 8-(1)

Preparation of polypeptide

The polypeptide was produced by culturing *Bacillus subtilis* MAU210 (FERM BP-2111) with a liquid culture medium similarly as in Example 10 and then purifying in accordance with the method in Example 4-(1) to obtain a high-purity polypeptide specimen.

On SDS polyacrylamide electrophoresis, the polypeptide specimen showed a molecular weight of $70,000 \pm 10,000$ daltons and a specific activity of $200 \pm 30$ units/mg protein.

EXAMPLE 8-(2)

N-terminal amino acid sequence

The partial amino acid sequence containing the N-terminal terminal end was determined with the polypeptide specimen prepared in Example 8-(1), in accordance with the method in Example 3-(2).

The partial amino acid sequence was Ser-Pro-Asp-Thr-Ser-Val-Asn-Asn-Lys-Leu.

EXAMPLE 9

Sequence of polypeptide gene derived from *Bacillus macerans* and amino acid sequence of polypeptide

EXAMPLE 9-(1)

Preparation of recombinant DNA carrying the polypeptide gene

The recombinant DNA was prepared in accordance with the method in Example 4-(3).

More particularly, a DNA fragment, obtained by digesting a DNA fragment carrying the polypeptide gene, prepared by the method in Example 7-(2), with restriction enzymes, and a plasmid fragment, obtained by cleaving a plasmid pUCI8 specimen, prepared by the method in Example 4-(2), in the same manner, were ligated with T4 DNA ligase to obtain a recombinant DNA.

EXAMPLE 9-(2)

Introduction of recombinant DNA into *Escherichia coli*

The recombinant DNA was introduced in accordance with the method in Example 4-(3) into *Escherichia coli* JM83 as the host microorganism to obtain a recombinant microorganism.

EXAMPLE 9-(3)

Preparation of recombinant DNA from recombinant microorganism

The recombinant DNA was prepared in accordance with the method in Example 4-(4).

EXAMPLE 9-(4)

Sequence of recombinant DNA

The polypeptide gene was sequenced in accordance with the method in Example 4-(5).

The results are as shown in FIG. 9.

The signal peptide located upstream of the 5'-site of the polypeptide gene was sequenced in the same manner.

The results are as shown in FIG. 10.

EXAMPLE 9-(5)

Amino acid sequence of polypeptide

The amino acid sequence of the polypeptide was determined with reference to the sequence of the polypeptide gene. The results are as shown in FIG. 12.

The amino acid sequence of the signal peptide was determined in the same manner. The results are as shown in FIG. 11.

This evidence confirms that the polypeptide derived from *Bacillus macerans* has the amino acid sequence as shown in FIG. 12.

The evidence as shown in FIGS. 8 and 12 show that each polypeptide has the following common amino acid sequences:

(a) Asn-Lys-Ile-Asn-Asp-Gly-Tyr-Leu-Thr,
(b) Pro-Val-Phe-Thr-Phe-Gly-Glu-Trp-Phe-Leu,
(c) Val-Thr-Phe-Ile-Asp-Asn-His-Asp-Mct-Asp-Arg-Phe,
(d) Ile-Tyr-Tyr-Gly-Thr-Glu-Gln-Tyr-Met-Thr-Gly-Asn-Gly-Asp-Pro-Asn-Asn-Arg, and
(e) Asn-Pro-Ala-Leu-Ala-Tyr-Gly, as well as that these partial amino acid sequences (a), (b), (c), (d) and (e) are located in order of nearness to the N-terminal end of the polypeptide. These common sequences are underlined in FIGS. 8 and 12.

EXAMPLE 10

Preparation of polypeptide with recombinant microorganism

Polypeptides were prepared with *Escherichia coli* MAH2 (FERM BP-2110) and *Bacillus subtilis* MAU210 (FERM BP-2111) both in which recombinant DNA carrying the polypeptide gene derived from *Bacillus macerans* had been introduced. The polypeptide productivities of these recombinant microorganisms, the host microorganisms without addition of the recombinant plasmid, and the donor *Bacillus macerans* microorganism were compared in relation to their CGTase activity. A liquid culture medium prepared by the method in Example 5 was used.

*Escherichia coli* MAH2 was inoculated to the liquid culture medium additionally containing 50 µg/ml of ampicillin, while *Escherichia coli* HB101 was inoculated to the liquid culture medium without addition of antibiotic. In each case, the microorganism was cultured at 35° C. for 24 hours under vigorous shaking conditions.

*Bacillus subtilis* MAU210 was inoculated to the liquid culture medium additionally containing 5 µg/ml of kanamycin, while *Bacillus subtilis* 715A was inoculated to the liquid culture medium without addition of antibiotic. In each case, microorganism was cultured at 28° C. for 72 hours.

*Bacillus macerans* 17A was cultured with the liquid culture medium at 28° C. for 72 hours without addition of antibiotic.

Each culture was treated similarly as in Example 5, and its CTGase activity was then determined. The results are as shown in Table 2.

TABLE 2

| Microorganism | CGTase activity (units/ml) | | | |
|---|---|---|---|---|
| | Supernatant | Cell | Total | |
| *Escherichia coli* MAH2 (FERM P-7925) | 0.6 | 11.8 | 12.4 | Present invention |
| *Bacillus subtilis* MAU210 (FERM P-7926) | 54.6 | 0.3 | 54.9 | Present invention |
| *Escherichi coli* HB101 | 0 | 0 | 0 | Control |
| *Bacillus subtilis* 715A | 0 | 0 | 0 | Control |
| *Bacillus macerans* 17A | 7.5 | 0.4 | 7.9 | Control |

This evidence clearly shows that the recombinant microorganisms are advantageously usable in industrial-scale production of polypeptide because they have an improved polypeptide productivity.

The supernatants were salted out with ammonium sulfate at a saturation degree of 0.6 to obtain crude polypeptide specimens.

On studying these crude polypeptide specimens on their enzymatic properties similarly as in Example 5, the enzymatic properties of the polypeptide produced by the recombinant microorganisms were in good accordance with those of the polypeptide produced by the donor *Bacillus macerans* microorganism.

Principal uses of the polypeptide will hereinafter be described.

The polypeptide effects the intra- or intermolecular saccharide transfer reaction between suitable saccharide donor and saccharide acceptor.

According to one aspect of the present invention, various saccharide-transferred products can be produced by taking advantage of these saccharide transfer reactions.

For example, a partial starch hydrolysate containing α-, β- and γ-cyclodextrins is prepared by subjecting an amylaceous substance as the substrate, such as starch, liquefied starch with a Dextrose Equivalent (DE) of below 10, or amylose, to the action of the polypeptide utilizing the intramolecular saccharide transfer reaction. Each cyclodextrin can be isolated from the partial starch hydrolysate, if necessary.

α-Glycosylated saccharide sweetener, for example, α-glycosyl-, α-maltosyl- and α-maltotriosyl-saccharides, is prepared by subjecting a mixture of a saccharide donor, for example, amylaceous substance such as starch, liquefied starch, dextrin, cyclodextrin or amylose; and a saccharide acceptor, for example, monosaccharide such as xylose, sorbose or fructose, or disaccharide such as sucrose, maltulose or isomaltulose, to the action of polypeptide utilizing the intermolecular saccharide transfer action. The α-glycosylated saccharide sweetener can be advantageously used in foods and beverages because the α-glycosylated saccharide sweetener is much milder in taste, more soluble in water, but less crystallizable in comparison with intact saccharide sweetener. These would expand extremely the use of saccharide sweeteners.

In the intermolecular saccharide transfer reaction, the use of a glycoside, for example, steviol glycoside such as stevioside or rebaudioside, glycyrrhizin, soyasaponin, teasaponin, rutin or esculin, as the saccharide acceptor leads to the formation of α-glycosylated glycosides such as α-glucosyl-, α-maltosyl- and α-maltotriosyl-glycosides. The α-glycosylated glycoside is free of the unpleasant tastes such as bitter- and astringent-tastes which are inherent to intact glycoside, and more readily soluble in water than intact glycoside. These would expand extremely the use of glycosides. Specifically, α-glycosylated steviol glycoside and α-glycosylated glycyrrhizin can be advantageously used in foods, beverages, and pharmaceuticals for peroral administration because the taste improvement in these α-glycosylated glycosides is remarkably high, as well as because their sweetness is comparable to that of sucrose.

Several embodiments will be disclosed.

EXAMPLE 11

Corn syrup containing cyclodextrin

A 10 w/w % suspension of potato starch was mixed with 2 units/g starch of a polypeptide specimen prepared with *Bacillus subtilis* TCU211 in accordance with the method in Example 5, liquefied by heating to 85° C. at pH 6.5, cooled to 70° C., further mixed with the same amount of the polypeptide specimen, and reacted for 40 hours. The reaction mixture was purified by decoloration using activated carbon and deionization using ion exchange resin, and then concentrated to obtain a starch syrup containing cyclodextrin in a yield of 92% based on the dry solid. The corn syrup can be advantageously incorporated into flavors and cosmetics wherein fragrance or aroma is one of the important factors because the corn syrup is excellent in flavor-locking properties.

The α-, β- and γ-cyclodextrins in the corn syrup can be separated by treating it with a procedure using organic precipitant, such as toluene or trichloromethane, or conventional column chromatography.

EXAMPLE 12

α-Glycosylsucrose

A 35 w/w % suspension of cornstarch was mixed with 0.2 w/w % oxalic acid, autoclaved to 120° C. to give a DE of 20, neutralized with calcium carbonate, and filtered to obtain a dextrin solution. The dextrin solution was then mixed with a half amount of sucrose based on the dry solid, and the resultant mixture was mixed with 15 units/g starch of a polypeptide specimen prepared with *Bacillus subtilis* MAU210 in accordance with the method in Example 10, and reacted at pH 6.0 and 55° C. for 40 hours. The reaction mixture was purified by decoloration using activated carbon and deionization using ion exchange resin, and then concentrated to obtain a colorless, transparent corn syrup in a yield of 94% based on the dry solid. The corn syrup containing a large amount of α-glycosylsucrose can be advantageously used in confectioneries because it is mildly sweet and amorphous.

EXAMPLE 13

α-Glycosyl stevioside

Two-hundred g of stevioside and 600 g of dextrin (DE 8) were dissolved in 3 liters of water by heating, and the resultant solution was cooled to 70° C., mixed with 5 units/g dextrin of a polypeptide specimen prepared with *Bacillus subtilis* TCU211 in accordance with the method in Example 5, and reacted at pH 6.0 and 65° C. for 35 hours. The reaction mixture was then heated to 95° C. for 15 minutes, purified by filtration, concentrated, and pulverized to obtain a pulverulent sweetener containing α-glycosyl stevioside in a yield of about 92% based on the dry solid.

The sweetener, free of the unpleasant taste which is inherent to intact stevioside, was comparable to sucrose in taste quality, and the sweetening power of the sweetener was about 100-fold higher than that of sucrose. The sweetener can be advantageously used as a diet sweetener or to season foods and beverages because of its low-cariogenic and low-calorific properties.

EXAMPLE 14

α-Glycosyl ginsenoside

Sixty g of a ginseng extract and 180 g of β-cyclodextrin were dissolved in 500 ml of water by heating, and the resultant mixture was cooled to 70° C., adjusted to pH 6.0, mixed with 3 units/g β-cyclodextrin of a polypeptide specimen prepared with *Escherichia coli* TCH201 in accordance with the method in Example 5, cooled to 65° C., and reacted to pH 6.0 for 40 hours. The reaction mixture was heated for 15 minutes to inactivate the polypeptide, followed by filtration. The filtrate was admitted to a column packed with 3 liters of "Amberlite XAD-7", a synthetic adsorbent commercialized by Rohm & Haas Co., Philadelphia, Pa., USA; thereafter, the column was sufficiently washed with water to remove free saccharides. To the column was then admitted 10 liters of 50 v/v % ethanol, and the eluate was concentrated and dehydrated to obtain about 21 g of a pulverulent product that contains α-glycosyl ginsenoside. Since the product is free of the unpleasant tastes such as bitter-, astringent- and harsh-tastes which are inherent to intact ginsenoside, the product can be perorally administered intact, or, if necessary, seasoned with any sweetener or sour, prior to its use. In addition, the product can be advantageously used in health foods and medicines for internal administration because the product possesses invigorating, peptic, intestine-regulating, haematic, anti-inflammatory and expectorant effects as intact ginsenoside does.

As described above, the present inventors determined the sequences of the CGTase polypeptide gene and its signal peptide, and prepared the recombinant DNA having a PvuII restriction site from a donor microorganism by in vitro genetic engineering techniques. Furthermore, the present inventors prepared recombinant microorganisms in which the recombinant DNA is introduced, as well as confirming that the recombinant microorganisms autonomically and consistently proliferate in a nutrient culture medium.

In view of adequately supplying polypeptide, the present invention is industrially significant because the present invention assures a wide polypeptide source and easily improves the polypeptide productivity of donor microorganisms.

While there has been described what is at present considered to be the preferred embodiments of the invention, it will be understood that various modifications may be made therein, and it is intended to cover in the appended claims all such modifications as fall within the true spirit and scope of the invention.

We claim:

1. A polypeptide possessing cyclomaltodextrin glucanotransferase (CGTase) activity, comprising one or more partial amino acid sequences selected from the group consising of (a) Asn-Lys-Ile-Asn-Asp-Gly-Tyr-Leu-Thr,
(b) Pro-Val-Phe-Thr-Phe-Gly-Glu-Tri-Phe-Leu,
(c) Val-Thr-Phe-Ile-Asp-Asn-His-Asp-Met-Asp-Arg-Phe,
(d) Ile-Tyr-Thr-Gly-Thr-Glu-Gln-Tyr-Met-Thr-Gly-Asn-Gly-Asp-Pro-Asn-Asn-Arg, and
(e) Asn-Pro-Ala-Leu-Ala-Tyr-Gly.

2. The polypeptide in accordance with claim 1,

3. The polypeptide in accordance with claim 1, which shows a molecular weight of 70,000±10,000 daltons on SDS-polyacrylamide electrophoresis.

4. The polypeptide in accordance with claim 1, whose N-terminal sequence is Ala-Gly-Asn-Leu-Asn-Lrs-Val-Asn-Phe-Thr.

5. The polypeptide in accordance with claim 4, which has the following amino acid sequence:

|       | 1   | 2   | 3   | 4   | 5   | 6   | 7   | 8   | 9   | 10  | 11  | 12  | 13  | 14  | 15  |
|-------|-----|-----|-----|-----|-----|-----|-----|-----|-----|-----|-----|-----|-----|-----|-----|
| 1>    | Ala | Gly | Asn | Leu | Asn | Lys | Val | Asn | Phe | Thr | Ser | Asp | Val | Val | Tyr |
| 16>   | Gln | Ile | Val | Val | Asp | Arg | Phe | Val | Asp | Gly | Asn | Thr | Ser | Asn | Asn |
| 31>   | Pro | Ser | Gly | Ala | Leu | Phe | Ser | Ser | Gly | Cys | Thr | Asn | Leu | Arg | Lys |
| 46>   | Tyr | Cys | Gly | Gly | Asp | Trp | Gln | Gly | Ile | Ile | Asn | Lys | Ile | Asn | Asp |
| 61>   | Gly | Tyr | Leu | Thr | Asp | Met | Gly | Val | Thr | Ala | Ile | Trp | Ile | Ser | Gln |
| 76>   | Pro | Val | Glu | Asn | Val | Phe | Ser | Val | Met | Asn | Asp | Ala | Ser | Gly | Ser |
| 91>   | Ala | Ser | Tyr | His | Gly | Tyr | Trp | Ala | Arg | Asp | Phe | Lys | Lys | Pro | Asn |
| 106>  | Pro | Phe | Phe | Gly | Thr | Leu | Ser | Asp | Phe | Gln | Arg | Leu | Val | Asp | Ala |
| 121>  | Ala | His | Ala | Lys | Gly | Ile | Lys | Val | Ile | Ile | Asp | Phe | Ala | Pro | Asn |
| 136>  | His | Thr | Ser | Pro | Ala | Ser | Glu | Thr | Asn | Pro | Ser | Tyr | Met | Glu | Asn |
| 151>  | Gly | Arg | Leu | Tyr | Asp | Asn | Gly | Thr | Leu | Leu | Gly | Gly | Tyr | Thr | Asn |
| 166>  | Asp | Ala | Asn | Met | Tyr | Phe | His | His | Asn | Gly | Gly | Thr | Thr | Phe | Ser |
| 181>  | Ser | Leu | Glu | Asp | Gly | Ile | Tyr | Arg | Asn | Leu | Phe | Asp | Leu | Ala | Asp |
| 196>  | Leu | Asn | His | Gln | Asn | Pro | Val | Ile | Asp | Arg | Tyr | Leu | Lys | Asp | Ala |
| 211>  | Val | Lys | Met | Trp | Ile | Asp | Met | Gly | Ile | Asp | Gly | Ile | Arg | Met | Asp |
| 226>  | Ala | Val | Lys | His | Met | Pro | Phe | Gly | Trp | Gln | Lys | Ser | Leu | Met | Asp |
| 241>  | Glu | Ile | Asp | Asn | Tyr | Arg | Pro | Val | Phe | Thr | Phe | Gly | Glu | Trp | Phe |
| 256>  | Leu | Ser | Glu | Asn | Glu | Val | Asp | Ala | Asn | Asn | His | Tyr | Phe | Ala | Asn |
| 271>  | Glu | Ser | Gly | Met | Ser | Leu | Leu | Asp | Phe | Arg | Phe | Gly | Gln | Lys | Leu |
| 286>  | Arg | Gln | Val | Leu | Arg | Asn | Asn | Ser | Asp | Asn | Trp | Tyr | Gly | Phe | Asn |
| 301>  | Gln | Met | Ile | Gln | Asp | Thr | Ala | Ser | Ala | Tyr | Asp | Glu | Val | Leu | Asp |
| 316>  | Gln | Val | Thr | Phe | Ile | Asp | Asn | His | Asp | Met | Asp | Arg | Phe | Met | Ile |
| 331>  | Asp | Gly | Gly | Asp | Pro | Arg | Lys | Val | Asp | Met | Ala | Leu | Ala | Val | Leu |
| 346>  | Leu | Thr | Ser | Arg | Gly | Val | Pro | Asn | Ile | Tyr | Tyr | Gly | Thr | Glu | Gln |
| 361>  | Tyr | Met | Thr | Gly | Asn | Gly | Asp | Pro | Asn | Asn | Arg | Lys | Met | Met | Ser |
| 376>  | Ser | Phe | Asn | Lys | Asn | Thr | Arg | Ala | Tyr | Gln | Val | Ile | Gln | Lys | Leu |
| 391>  | Ser | Ser | Leu | Arg | Arg | Asn | Asn | Pro | Ala | Leu | Ala | Tyr | Gly | Asp | Thr |
| 406>  | Glu | Gln | Arg | Trp | Ile | Asn | Gly | Asp | Val | Tyr | Val | Tyr | Glu | Arg | Gln |
| 421>  | Phe | Gly | Lys | Asp | Val | Val | Leu | Val | Arg | Val | Asn | Arg | Ser | Ser | Ser |
| 436>  | Ser | Asn | Tyr | Ser | Ile | Thr | Gly | Leu | Phe | Thr | Ala | Leu | Pro | Ala | Gly |
| 451>  | Thr | Tyr | Thr | Asp | Gln | Leu | Gly | Gly | Leu | Leu | Asp | Gly | Asn | Thr | Ile |
| 466>  | Gln | Val | Gly | Ser | Asn | Gly | Ser | Val | Asn | Ala | Phe | Asp | Leu | Gly | Pro |
| 481>  | Gly | Glu | Val | Gly | Val | Trp | Ala | Tyr | Ser | Ala | Thr | Glu | Ser | Thr | Pro |
| 496>  | Ile | Ile | Gly | His | Val | Gly | Pro | Met | Met | Gly | Gln | Val | Gly | His | Gln |
| 511>  | Val | Thr | Ile | Asp | Gly | Glu | Gly | Phe | Gly | Thr | Asn | Thr | Gly | Thr | Val |
| 526>  | Lys | Phe | Gly | Thr | Thr | Ala | Ala | Asn | Val | Val | Ser | Trp | Ser | Asn | Asn |
| 541>  | Gln | Ile | Val | Val | Ala | Val | Pro | Asn | Val | Ser | Pro | Gly | Lys | Tyr | Asn |
| 556>  | Ile | Thr | Val | Gln | Ser | Ser | Ser | Gly | Gln | Thr | Ser | Ala | Ala | Tyr | Asp |
| 571>  | Asn | Phe | Glu | Val | Leu | Thr | Asn | Asp | Gln | Val | Ser | Val | Arg | Phe | Val |
| 586>  | Val | Asn | Asn | Ala | Thr | Thr | Asn | Leu | Gly | Gln | Asn | Ile | Tyr | Ile | Val |
| 601>  | Gly | Asn | Val | Tyr | Glu | Leu | Gly | Asn | Trp | Asp | Thr | Ser | Lys | Ala | Ile |
| 616>  | Gly | Pro | Met | Phe | Asn | Gln | Val | Val | Tyr | Ser | Tyr | Pro | Thr | Trp | Tyr |
| 631>  | Ile | Asp | Val | Ser | Val | Pro | Glu | Gly | Lys | Thr | Ile | Glu | Phe | Lys | Phe |
| 646>  | Ile | Lys | Lys | Asp | Ser | Gln | Gly | Asn | Val | Thr | Trp | Glu | Ser | Gly | Ser |
| 661>  | Asn | His | Val | Tyr | Thr | Thr | Pro | Thr | Asn | Thr | Thr | Gly | Lys | Ile | Ile |
| 676>  | Val | Asp | Trp | Gln | Asn |     |     |     |     |     |     |     |     |     |     | wherein said partial amino acid sequences of
(a) Asn-Lys-Ile-Asn-Asp-Gly-Tyr-Leu-Thr,
(b) Pro-Val-Phe-Thr-Phe-Gly-Glu-Trp-Phe-Leu,
(c) Val-Thr-Phe-Ile-Asp-Asn-His-Asp-Met-Asp-Arg-Phe,
(d) Ile-Tyr-Tyr-Gly-Thr-Glu-Gln-Tyr-Met-Thr-Gly-Asn-Gly-Asp-Pro-Asn-Asn-Arg, and
(e) Asn-Pro-Ala-Leu-Ala-Tyr-Gly
are located in order or relative nearness to the N-terminal end of said polypeptide, such that (a) is nearer to the N-terminal end than (b), (b) is nearer than (c), (c) is nearer than (d) and (d) is nearer than (e).

6. The polypeptide in accordance with claim 4, wherein a signal peptide having an amino acid sequence of Met-Arg-Arg-Trp-Leu-Ser-Leu-Val-Leu-Ser-Met-Ser-Phe-Val-Phe-Ser-Ala-Ile-Phe-Ile-Val-Ser-Asp-Thr-Gln-Lys-Val-Thr-Val-Glu-Ala is located upstream at the N-terminal side of said polypeptide.

7. The polypeptide in accordance with claim 1, whose N-terminal sequence is Ser-Pro-Asp-Thr-Ser-Val-Asn-Asn-Lys-Leu.

8. The polypeptide in accordance with claim 1, which has the following amino acid sequence;

|      | 1   | 2   | 3   | 4   | 5   | 6   | 7   | 8   | 9   | 10  | 11  | 12  | 13  | 14  | 15  |
|------|-----|-----|-----|-----|-----|-----|-----|-----|-----|-----|-----|-----|-----|-----|-----|
| 1>   | Ser | Pro | Asp | Thr | Ser | Val | Asn | Asn | Lys | Leu | Asn | Phe | Ser | Thr | Asp |
| 16>  | Thr | Val | Tyr | Gln | Ile | Val | Thr | Asp | Arg | Phe | Val | Asp | Gly | Asn | Ser |
| 31>  | Ala | Asn | Asn | Pro | Thr | Gly | Ala | Ala | Phe | Ser | Ser | Asp | His | Ser | Asn |
| 46>  | Leu | Lys | Leu | Tyr | Phe | Gly | Gly | Asp | Trp | Gln | Gly | Ile | Thr | Asn | Lys |

-continued

|  | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 61> | Ile | Asn | Asp | Gly | Tyr | Leu | Thr | Gly | Met | Gly | Ile | Thr | Ala | Leu | Trp |
| 76> | Ile | Ser | Gln | Pro | Val | Gly | Asn | Ile | Thr | Ala | Val | Ile | Asn | Tyr | Ser |
| 91> | Gly | Val | Asn | Asn | Thr | Ala | Tyr | His | Gly | Tyr | Trp | Pro | Arg | Asp | Phe |
| 106> | Lys | Lys | Thr | Asn | Ala | Ala | Phe | Gly | Ser | Phe | Thr | Asp | Phe | Ser | Asn |
| 121> | Leu | Ile | Ala | Ala | Ala | His | Ser | His | Asn | Ile | Lys | Val | Val | Met | Asp |
| 136> | Phe | Ala | Pro | Asn | His | Thr | Asn | Pro | Ala | Ser | Ser | Thr | Asp | Pro | Ser |
| 151> | Phe | Ala | Glu | Asn | Gly | Ala | Leu | Tyr | Asn | Asn | Gly | Thr | Leu | Leu | Gly |
| 166> | Lys | Tyr | Ser | Asn | Asp | Thr | Ala | Gly | Leu | Phe | His | His | Asn | Gly | Gly |
| 181> | Thr | Asp | Phe | Ser | Thr | Thr | Glu | Ser | Gly | Ile | Tyr | Lys | Asn | Leu | Tyr |
| 196> | Asp | Leu | Ala | Asp | Ile | Asn | Gln | Asn | Asn | Asn | Thr | Ile | Asp | Ser | Tyr |
| 211> | Leu | Lys | Glu | Ser | Ile | Gln | Leu | Trp | Leu | Asn | Leu | Gly | Val | Asp | Gly |
| 226> | Ile | Arg | Phe | Asp | Ala | Val | Lys | His | Met | Pro | Gln | Gly | Trp | Gln | Lys |
| 241> | Ser | Tyr | Val | Ser | Ser | Ile | Tyr | Ser | Ser | Ala | Asn | Pro | Val | Phe | Thr |
| 256> | Phe | Gly | Glu | Trp | Phe | Leu | Gly | Pro | Asp | Glu | Met | Thr | Gln | Asp | Asn |
| 271> | Ile | Asn | Phe | Ala | Asn | Gln | Ser | Gly | Met | His | Leu | Leu | Asp | Phe | Ala |
| 286> | Phe | Ala | Gln | Glu | Ile | Arg | Glu | Val | Phe | Arg | Asp | Lys | Ser | Glu | Thr |
| 301> | Met | Thr | Asp | Leu | Asn | Ser | Val | Ile | Ser | Ser | Thr | Gly | Ser | Ser | Tyr |
| 316> | Asn | Tyr | Ile | Asn | Asn | Met | Val | Thr | Phe | Ile | Asp | Asn | His | Asp | Met |
| 331> | Asp | Arg | Phe | Gln | Gln | Ala | Gly | Ala | Ser | Thr | Arg | Pro | Thr | Glu | Gln |
| 346> | Ala | Leu | Ala | Val | Thr | Leu | Thr | Ser | Arg | Gly | Val | Pro | Ala | Ile | Tyr |
| 361> | Tyr | Gly | Thr | Glu | Gln | Tyr | Met | Thr | Gly | Asn | Gly | Asp | Pro | Asn | Asn |
| 376> | Arg | Gly | Met | Met | Thr | Gly | Phe | Asp | Thr | Asn | Lys | Thr | Ala | Tyr | Lys |
| 391> | Val | Ile | Lys | Ala | Leu | Ala | Pro | Leu | Arg | Lys | Ser | Asn | Pro | Ala | Leu |
| 406> | Ala | Tyr | Gly | Ser | Thr | Thr | Gln | Arg | Trp | Val | Asn | Ser | Asp | Val | Tyr |
| 421> | Val | Tyr | Glu | Arg | Lys | Phe | Gly | Ser | Asn | Val | Ala | Leu | Val | Ala | Val |
| 436> | Asn | Arg | Ser | Ser | Thr | Thr | Ala | Tyr | Pro | Ile | Ser | Gly | Ala | Leu | Thr |
| 451> | Ala | Leu | Pro | Asn | Gly | Thr | Tyr | Thr | Asp | Val | Leu | Gly | Gly | Leu | Leu |
| 466> | Asn | Gly | Asn | Ser | Ile | Thr | Val | Asn | Gly | Gly | Thr | Val | Ser | Asn | Phe |
| 481> | Thr | Leu | Ala | Ala | Gly | Gly | Thr | Ala | Val | Trp | Gln | Tyr | Thr | Thr | Thr |
| 496> | Glu | Ser | Ser | Pro | Ile | Ile | Gly | Asn | Val | Gly | Pro | Thr | Met | Gly | Lys |
| 511> | Pro | Gly | Asn | Thr | Ile | Thr | Ile | Asp | Gly | Arg | Gly | Phe | Gly | Thr | Thr |
| 526> | Lys | Asn | Lys | Val | Thr | Phe | Gly | Thr | Thr | Ala | Val | Thr | Gly | Ala | Asn |
| 541> | Ile | Val | Ser | Trp | Glu | Asp | Thr | Glu | Ile | Lys | Val | Lys | Val | Pro | Asn |
| 556> | Val | Ala | Ala | Gly | Asn | Thr | Ala | Val | Thr | Val | Thr | Asn | Ala | Ala | Gly |
| 571> | Thr | Thr | Ser | Ala | Ala | Phe | Asn | Asn | Phe | Asn | Val | Leu | Thr | Ala | Asp |
| 586> | Gln | Val | Thr | Val | Arg | Phe | Lys | Val | Asn | Asn | Ala | Thr | Thr | Ala | Leu |
| 601> | Gly | Gln | Asn | Val | Tyr | Leu | Thr | Gly | Asn | Val | Ala | Glu | Leu | Gly | Asn |
| 616> | Trp | Thr | Ala | Ala | Asn | Ala | Ile | Gly | Pro | Met | Tyr | Asn | Gln | Val | Glu |
| 631> | Ala | Ser | Tyr | Pro | Thr | Trp | Tyr | Phe | Asp | Val | Ser | Val | Pro | Ala | Asn |
| 646> | Thr | Ala | Leu | Gln | Phe | Lys | Phe | Ile | Lys | Val | Asn | Gly | Ser | Thr | Val |
| 661> | Thr | Trp | Glu | Gly | Gly | Asn | Asn | His | Thr | Phe | Thr | Ser | Pro | Ser | Ser |
| 676> | Gly | Val | Ala | Thr | Val | Thr | Val | Asp | Trp | Gln | Asn |  |  |  |  |

9. The polypeptide in accordance with claim 8, wherein a signal peptide having an amino acid sequence of Met-Lys-Lys-Gln-Val-Lys-Trp-Leu-Thr-Ser-Val-Ser-Met-Ser-Val-Gly-Ile-Ala-Leu-Gly-Ala-Ala-Leu-Pro-Val-Trp-Ala is located upstream at the N-terminal side of said polypeptide.

10. The polypeptide in accordance with claim 1, produced by a microorganism of species *Bacillus stearothermophilus*.

11. The polypeptide in accordance with claim 1, produced by a microorganism of species *Bacillus macerans*.

12. The polypeptide in accordance with claim 1, produced by a recombinant microorganism in which a recombinant DNA carrying CGTase gene has been introduced.

13. A process for producing a polypeptide in accordance with claim 1, comprising:
culturing with a nutrient culture medium a recombinant microorganism having a recombinant DNA carrying isolated structural and promoter genes coding for the expression of said polypeptide; and recovering the accumulated polypeptide.

14. The process in accordance with claim 13, wherein said recombinant microorganism is of the genus Escherichia or Bacillus.

15. The process in accordance with claim 13, wherein said recombinant microorganism is a member selected from the group consisting of *Escherichia coli* TCH201 (FERM BP-2109) or *Escherichia coli* MAH2 (FERM BP-2110).

16. The process in accordance with claim 13, wherein said recombinant microorganism is a member selected from the group consisting of *Bacillus subtilis* MAU210 (FERM BP-2111) and *Bacillus subtilis* TCU211 (FERM BP-2112).

17. DNA consisting essentially of DNA coding for a polypeptide possessing cyclomaltodextrin glucanotransferase (CGTase) activity, comprising one or more partial amino acid sequences selected from the group consisting of
(a) Asn-Lys-Ile-Asn-Asp-Gly-Tyr-Leu-Thr,
(b) Pro-Val-Phe-Thr-Phe-Gly-Glu-Trp-Phe-Leu,
(c) Val-Thr-Phe-Ile-Asp-Asn-His-Asp-Met-Asp-Arg-Phe,
(d) Ile-Tyr-Tyr-Gly-Thr-Glu-Gln-Tyr-Met-Thr-Gly-Asn-Gly-Asp-Pro-Asn-Asn-Arg, and
(e) Asn-Pro-Ala-Leu-Ala-Tyr-Gly.

18. DNA consisting essentially of DNA coding for the polypeptide in accordance with claim 5.

19. DNA consisting essentially of DNA coding for the polypeptide in accordance with claim 8.

20. DNA in accordance with claim 17, wherein said DNA is recombinant DNA carrying isolated structural and promoter genes coding for the expression of said polypeptide, wherein said structural and promoter genes have been isolated from a donor microorganism of the genus Bacillus.

21. The recombinant DNA in accordance with claim 20, wherein said donor microorganism is of the species *Bacillus stearothermophilus*.

22. A biologically-pure culture of a recombinant microorganism having a recombinant DNA which includes DNA in accordance with claim 17.

23. The culture in accordance with claim 22, wherein said recombinant microorganism is of genus Escherichia or Bacillus.

24. The culture in accordance with claim 22, wherein said recombinant microorganism is a member selected from the group consisting of *Escherichia coli* TCH201 (FERM BP-2109) or *Escherichia coli* MAH2 (FERM BP-2110).

25. The culture in accordance with claim 22, wherein said recombinant microorganism is a member selected from the group consisting of *Bacillus subtilis* MAU210 (FERM BP-2111) and *Bacillus subtilis* TCU211 (FERM BP-2112).

* * * * *